United States Patent
Akagi et al.

(10) Patent No.: US 11,759,470 B2
(45) Date of Patent: Sep. 19, 2023

(54) SUSPENSION FOR ORAL ADMINISTRATION COMPRISING AMORPHOUS TOLVAPTAN

(71) Applicant: OTSUKA PHARMACEUTICAL CO., LTD., Tokyo (JP)

(72) Inventors: Akitsuna Akagi, Osaka (JP); Kai Suzuki, Osaka (JP); Atsuya Nakamura, Osaka (JP); Toru Nishibayashi, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 80 days.

(21) Appl. No.: 14/770,563

(22) PCT Filed: Feb. 28, 2014

(86) PCT No.: PCT/JP2014/055890
§ 371 (c)(1),
(2) Date: Aug. 26, 2015

(87) PCT Pub. No.: WO2014/133196
PCT Pub. Date: Sep. 4, 2014

(65) Prior Publication Data
US 2016/0000801 A1    Jan. 7, 2016

(30) Foreign Application Priority Data
Mar. 1, 2013 (JP) .................................. 2013-041105

(51) Int. Cl.
| | | |
|---|---|---|
| *A61K 31/55* | (2006.01) | |
| *A61K 47/38* | (2006.01) | |
| *A61K 9/00* | (2006.01) | |
| *A61K 9/16* | (2006.01) | |
| *A61K 47/26* | (2006.01) | |
| *A61K 9/10* | (2006.01) | |

(52) U.S. Cl.
CPC ............ *A61K 31/55* (2013.01); *A61K 9/0053* (2013.01); *A61K 9/0095* (2013.01); *A61K 9/10* (2013.01); *A61K 9/1652* (2013.01); *A61K 47/26* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 9,597,283 B2* | 3/2017 | Kaneko ................. | A61K 9/0019 |
| 2008/0260837 A1* | 10/2008 | Namburi .................. | A61K 9/10 |
| | | | 424/488 |
| 2010/0233265 A1 | 9/2010 | Suzuki et al. | |
| 2013/0102588 A1* | 4/2013 | Wu .......................... | A61K 9/10 |
| | | | 514/213.01 |

FOREIGN PATENT DOCUMENTS

| | | |
|---|---|---|
| JP | 04-154765 A | 5/1992 |
| JP | 11-021241 A | 1/1999 |
| KR | 10-2010-0092944 A | 8/2010 |
| WO | 91/05549 A1 | 5/1991 |
| WO | 2008/156217 A2 | 12/2008 |
| WO | 2009/001968 A1 | 12/2008 |
| WO | 2009/051022 A2 | 4/2009 |
| WO | 2009/056980 A1 | 5/2009 |
| WO | 2010/026971 A1 | 3/2010 |
| WO | 2011/160541 A1 | 12/2011 |
| WO | 2012/085071 A1 | 6/2012 |
| WO | WO 2014/104412 A1 * | 7/2014 |

OTHER PUBLICATIONS

Merriam-Webster Dictionary [Online]. "Syrup". [Retrieved Oct. 10, 2017]. Retrieved from the Internet: <URL: http://www.merriam-webster.com/dictionary/syrup>. (Year: 2017).*
European Medicines Agency. "CHMP Assessment Report for SAMSCA". European Medicines Agency (Evaluation of Medicines for Human Use). 2009. (Year: 2009).*
International Search Report of PCT/JP2014/055890 dated May 30, 2014 [PCT/ISA/210].
Written Opinion of PCT/JP2014/055890 dated May 30, 2014 [PCT/ISA/237].
Communication dated Feb. 13, 2018 from the Japanese Patent Office in counterpart application No. 2015-543171.
Sato, "Diuretic management for heart failure-perspectives regarding vasopressin antagonist", Journal of Clinical and Experimental Medicine, vol. 243, No. 3, Oct. 23, 2012, pp. 241-244.
Watanabe et al., "Short-term effects of low-dose tolvaptan on hemodynamic parameters in patients with chronic heart failure", Journal of Cardiology, vol. 60, 2012, pp. 462-469.
Momomura, "Relationship between diuretics and heart failure", Fluid Management Renaissance, vol. 1, No. 1, 2011, pp. 25-31.
Office Action dated Sep. 26, 2017 issued by the Japanese Patent Office in counterpart Japanese Application No. 2015-543171.

* cited by examiner

*Primary Examiner* — Leslie A. Royds Draper
(74) *Attorney, Agent, or Firm* — Sughrue Mion, PLLC

(57) ABSTRACT

This invention provides a suspension for oral administration comprising particles containing amorphous tolvaptan that can inhibit or delay crystallization of amorphous tolvaptan over time in the suspension, and stably maintain high solubility of tolvaptan and excellent absorbability of tolvaptan from the gastrointestinal tract; and a solid formulation for oral administration that can be suspended to prepare the suspension for oral administration at the time of use.
This invention relates to a suspension for oral administration, in particular, a syrup, comprising (a) particles containing amorphous tolvaptan, (b) hydroxypropyl methylcellulose (HPMC), and (c) a solvent, wherein the amount of the HPMC (b) is 0.1 to 25% by weight based on the total weight of the suspension for oral administration.

21 Claims, 13 Drawing Sheets
(11 of 13 Drawing Sheet(s) Filed in Color)

[Fig. 1]
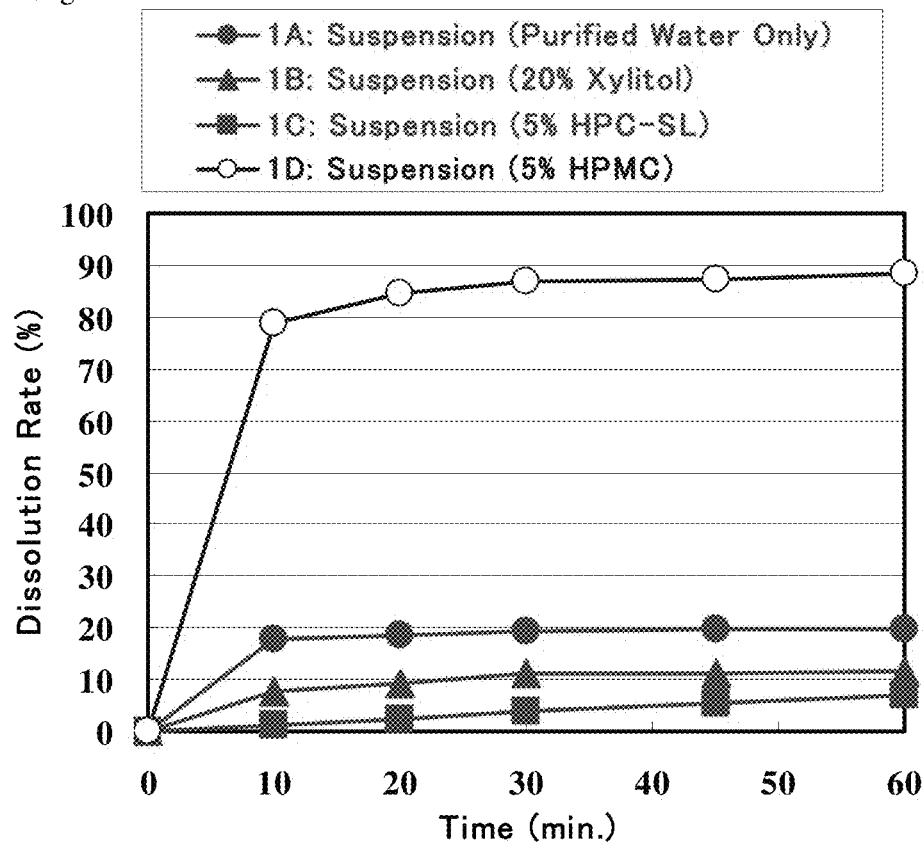

[Fig. 2]
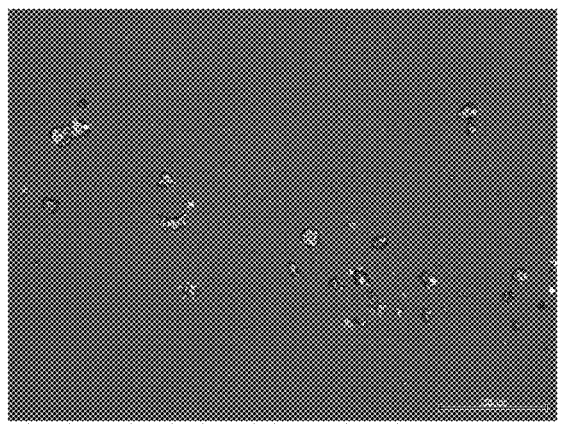 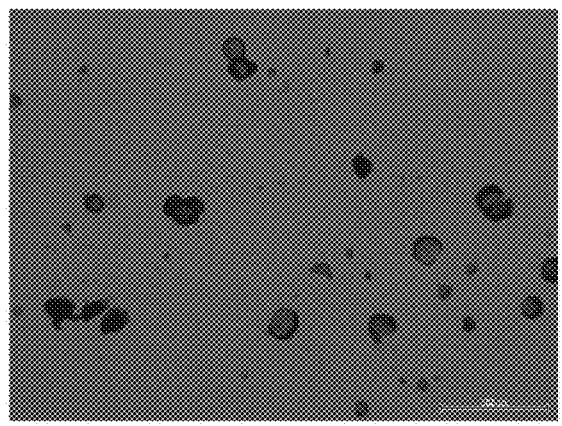
Crystallization
Polarizing microscope
Photograph x100
Preparation Example 1C
(After Storage)
Remaining Amorphous
Polarizing microscope
Photograph x100
Preparation Example 1D
(After Storage)

[Fig. 3-1]
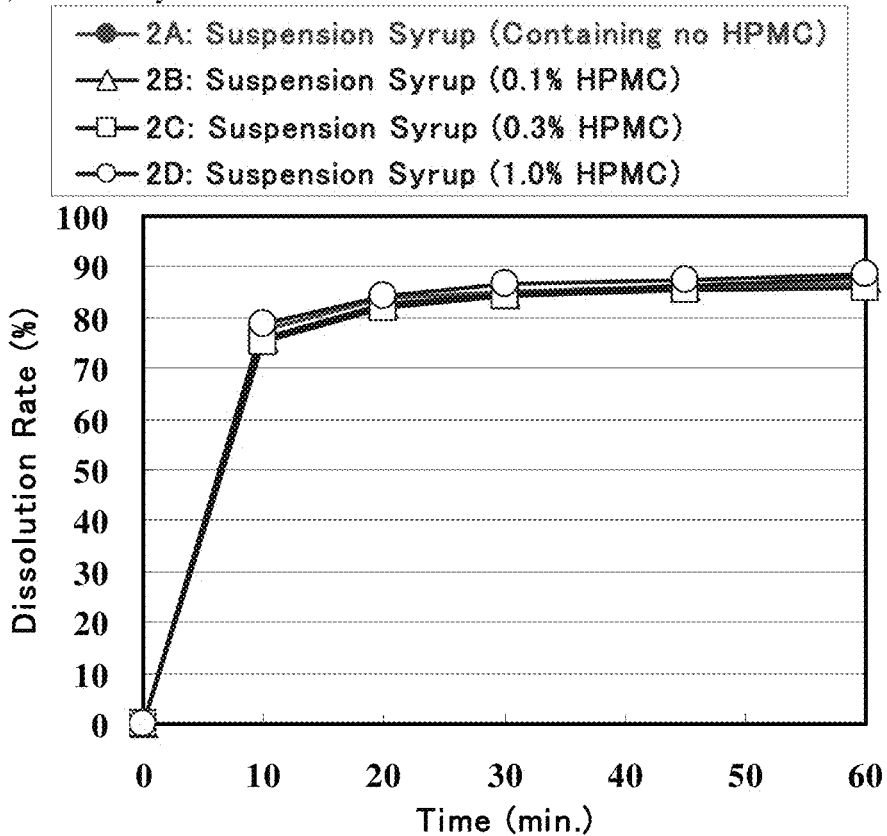

[Fig. 3-2]
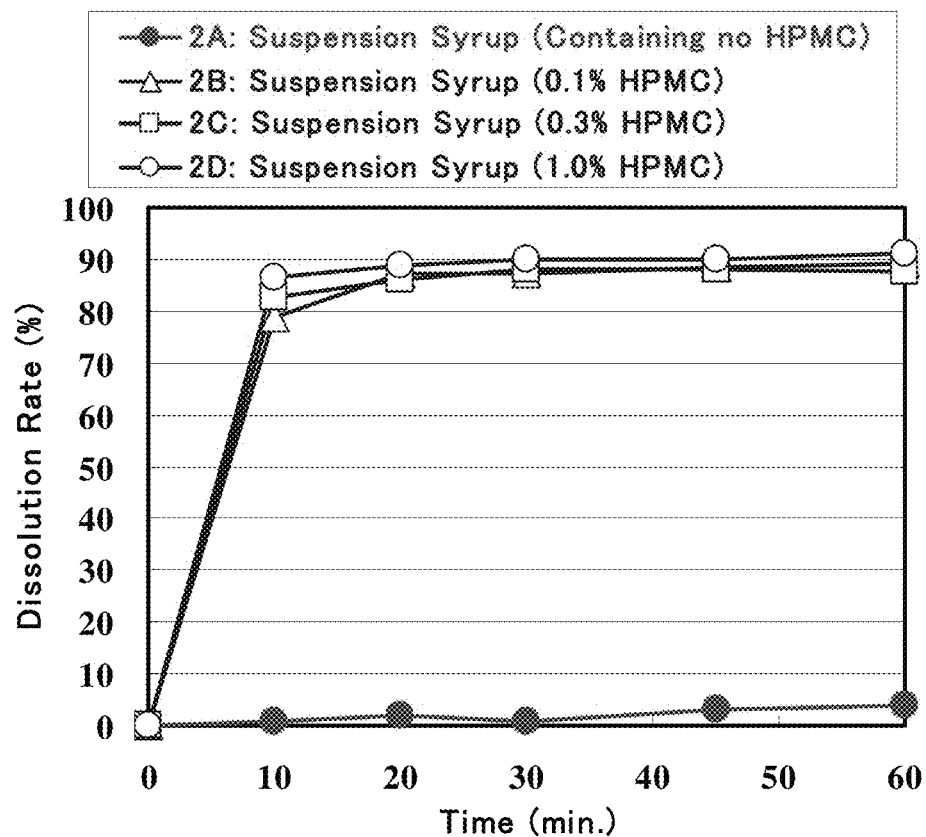

[Fig. 4]
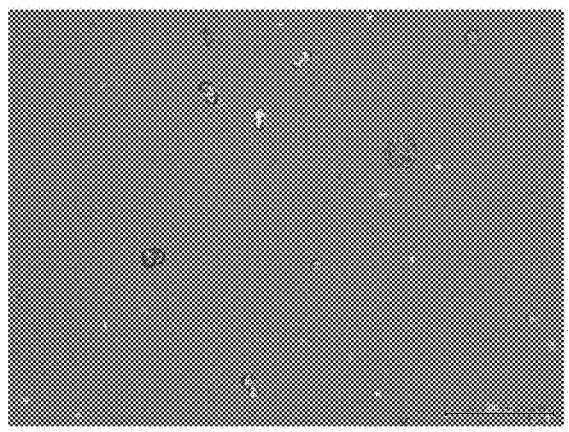
Crystallization
Polarizing Microscope
Photograph x 100
Preparation Example 2A
(After Storage)
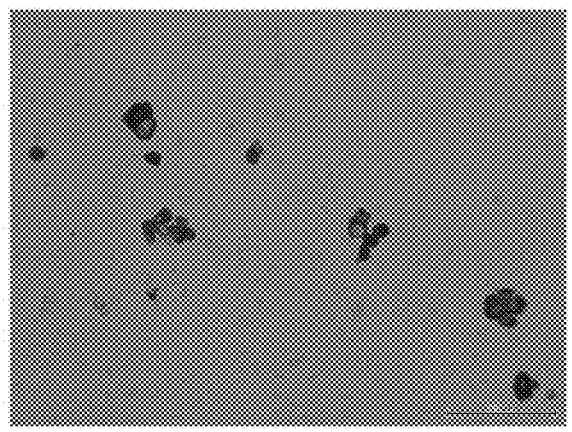
Remaining Amorphous
Polarizaing Microscope
Photograph x 100
Preparation Example 2B
(After Storage)

[Fig. 5]
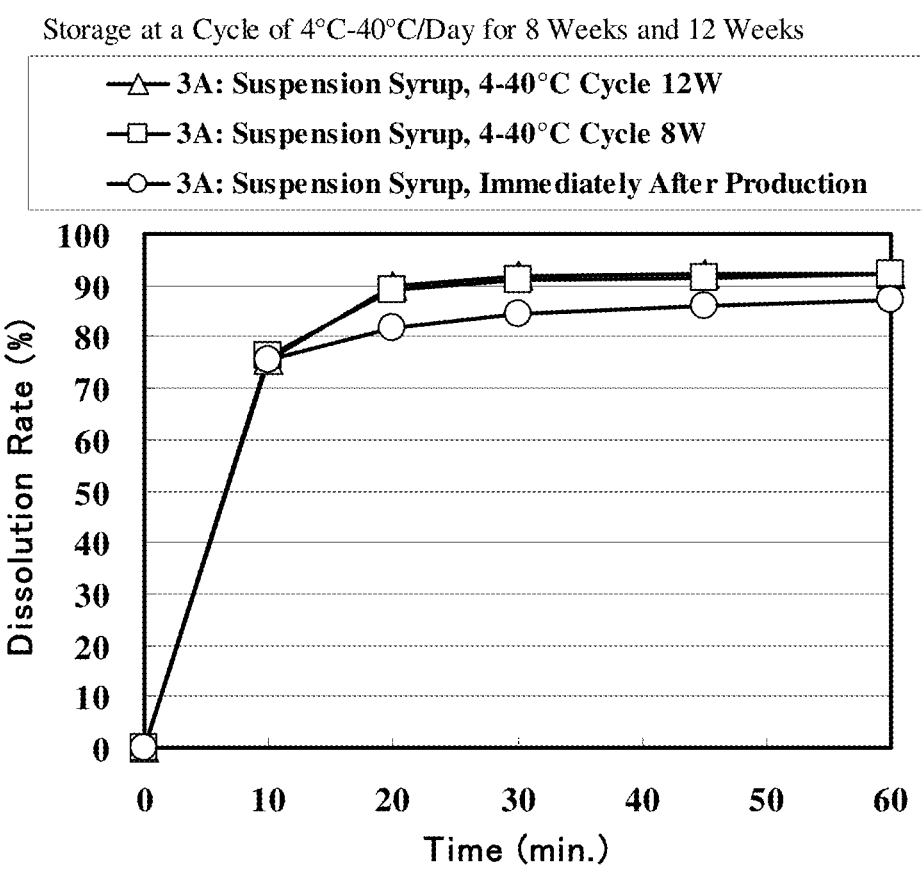

[Fig. 6]
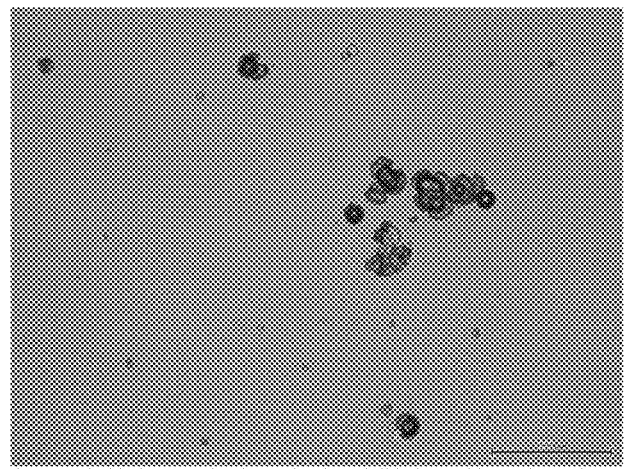
Remaining Amorphous
Polarizing Microscope Photograph × 100
Preparation Example 3A
(After Storage for 12W)

[Fig. 7]
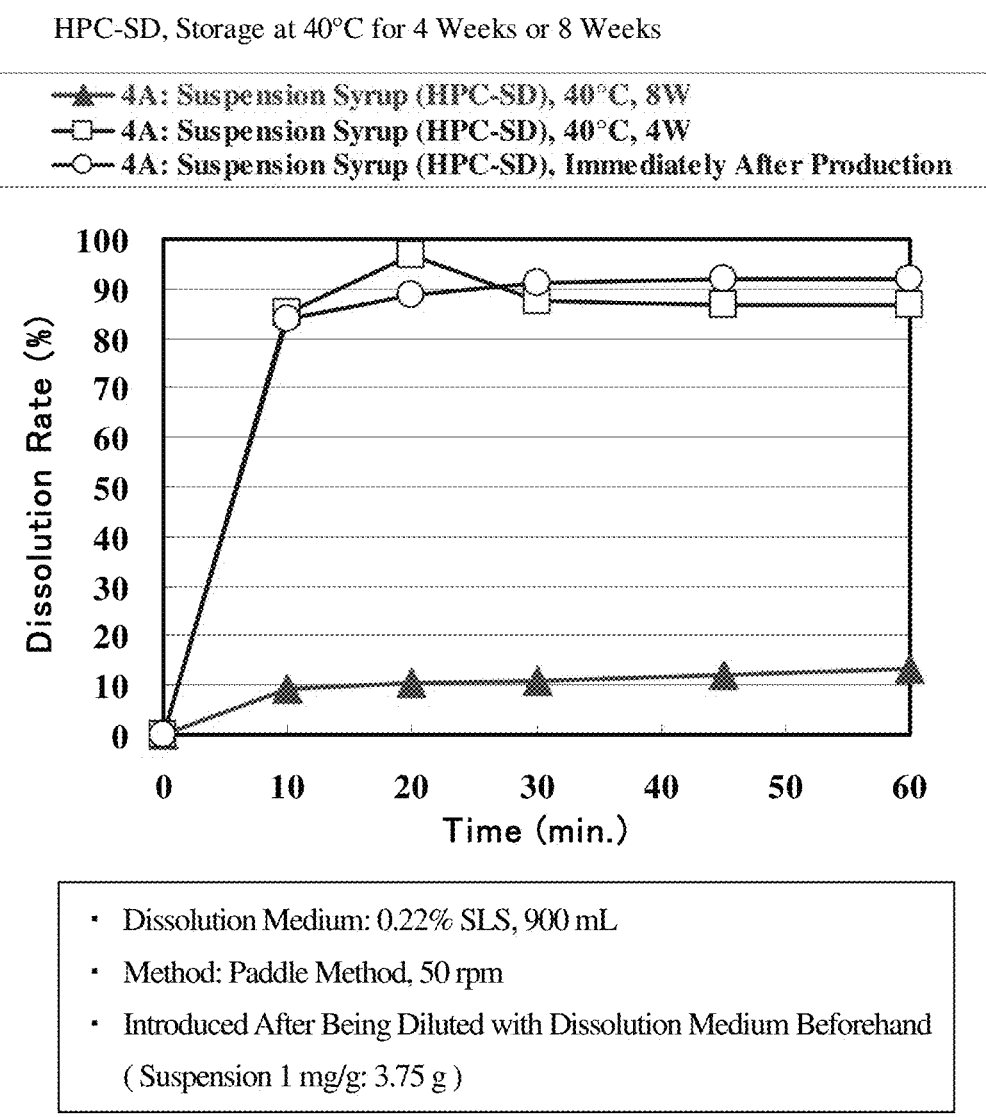

[Fig. 8]
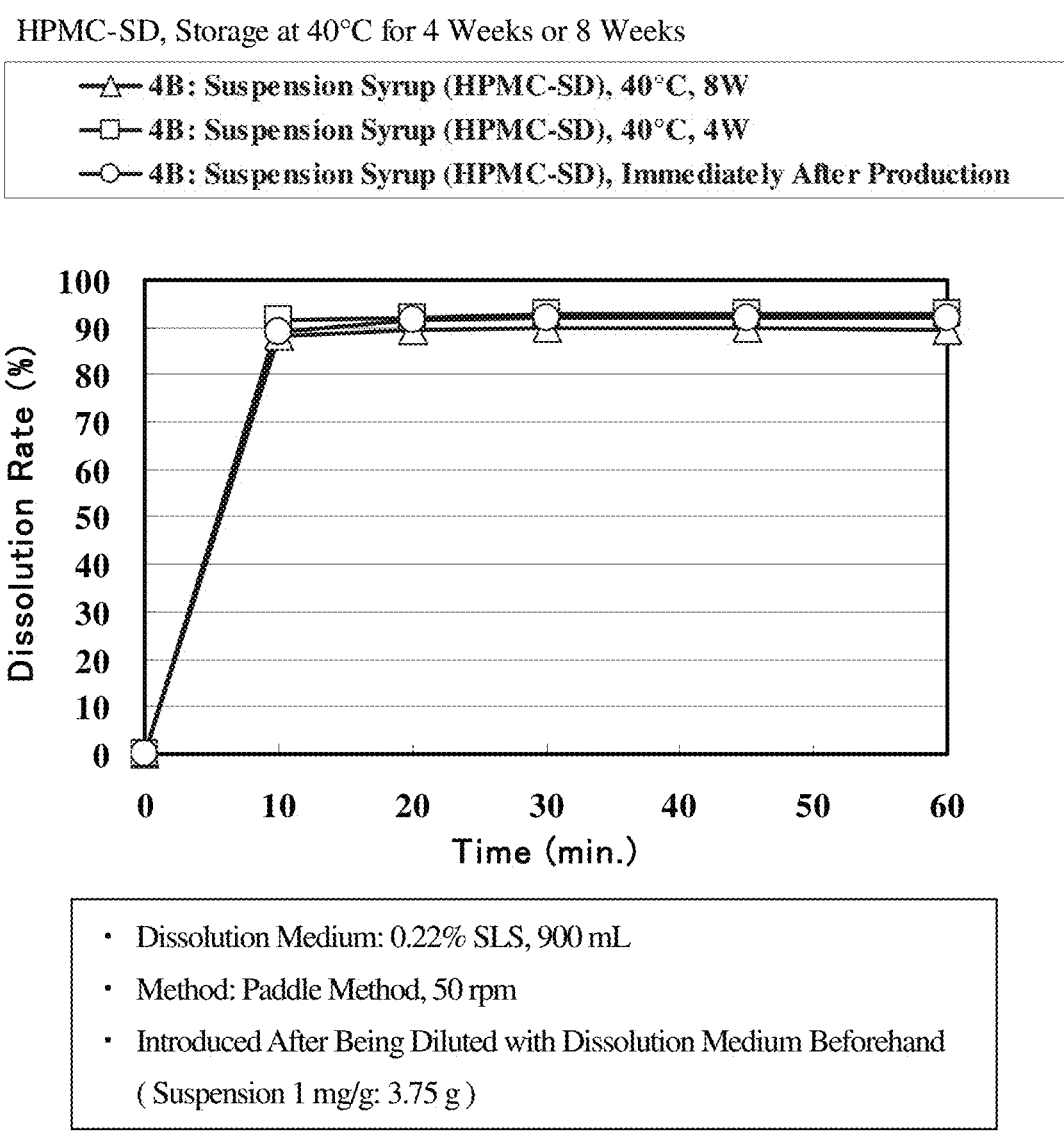

[Fig. 9]
(1) Dissolution Profiles
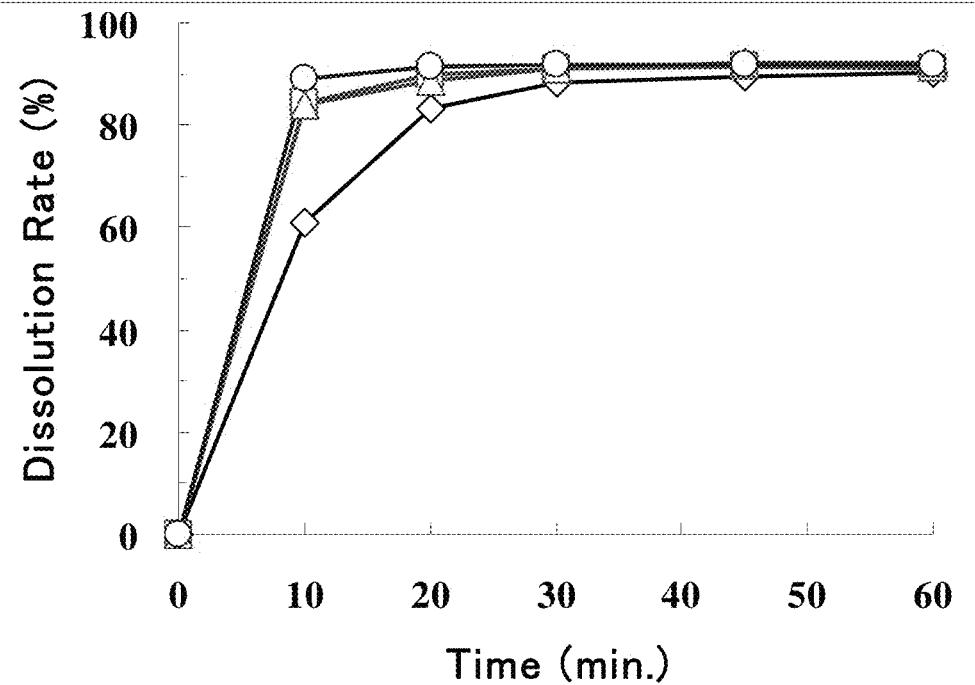
- Dissolution Medium: 0.22% SLS, 900 mL
- Method: Paddle Method, 50 rpm
- Introduced After Being Diluted with Dissolution Medium Beforehand
  ( Suspension Syrup 1 mg/g: 3.75 g )

[Fig. 10]
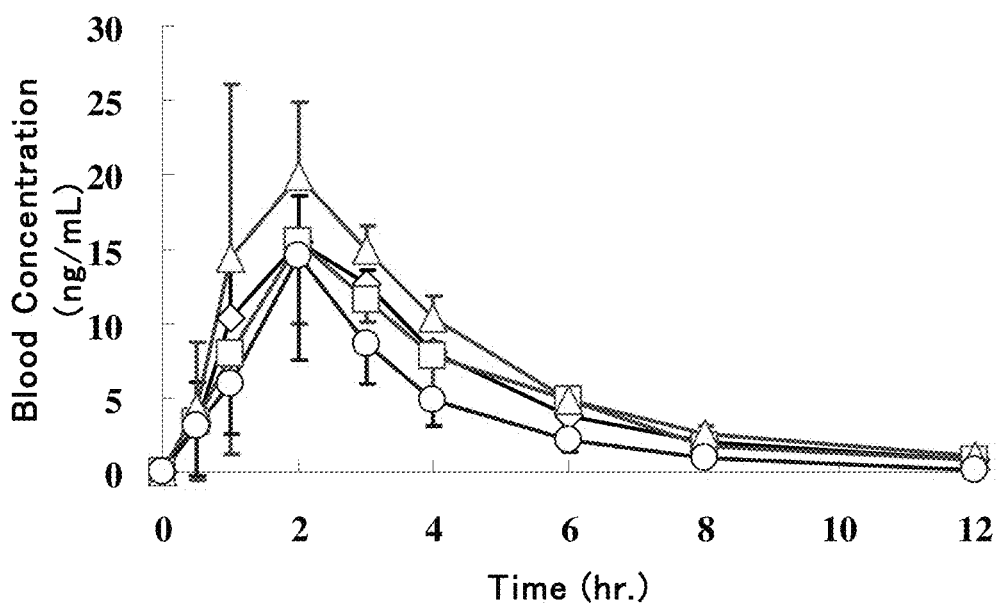

[Fig. 11]
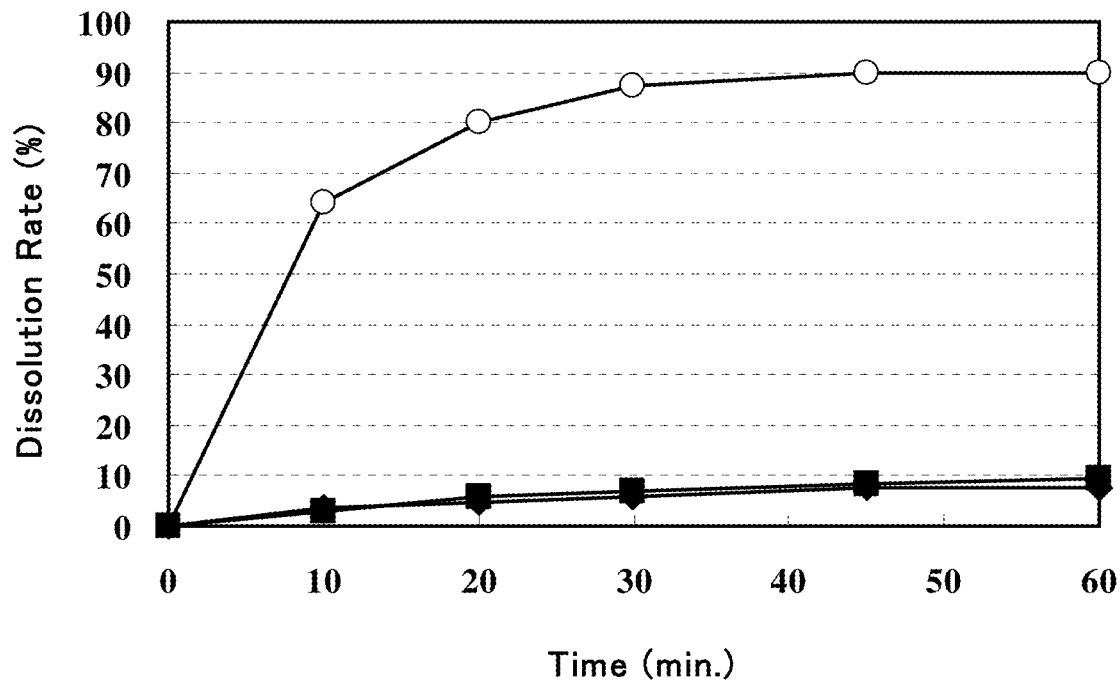

[Fig. 12(a)]
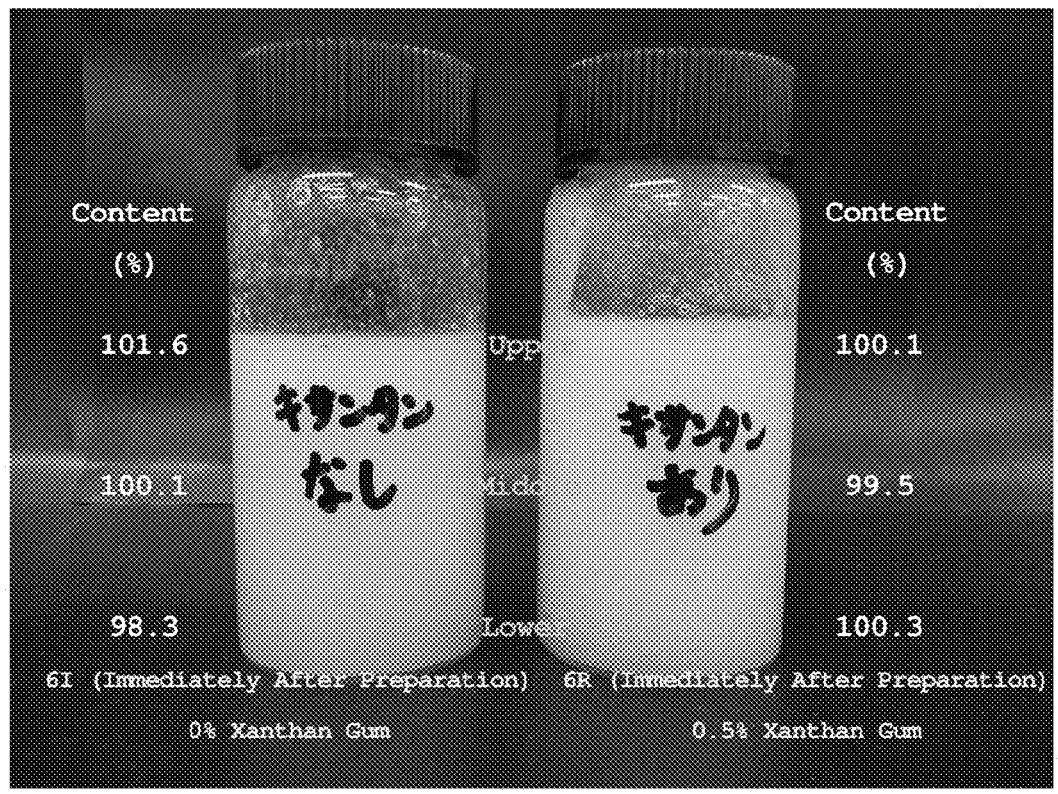
[Fig. 12(b)]
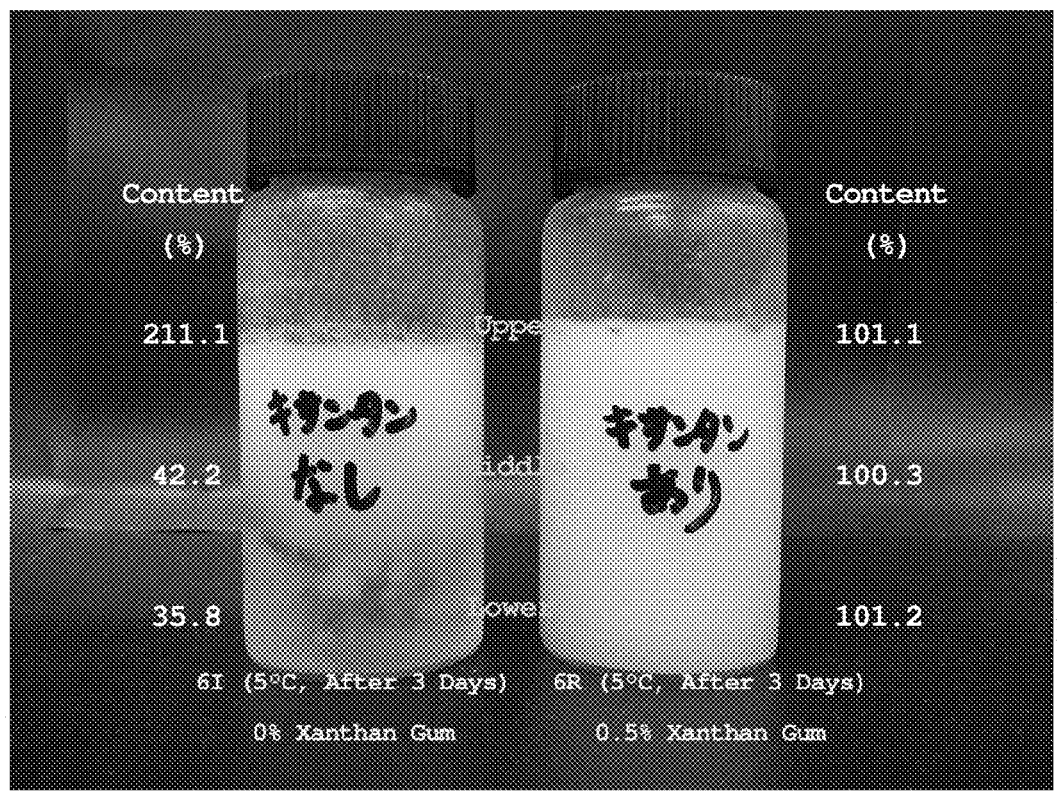

SUSPENSION FOR ORAL ADMINISTRATION COMPRISING AMORPHOUS TOLVAPTAN

CROSS REFERENCE TO RELATED APPLICATIONS

This application is a National Stage of International Application No. PCT/JP2014/055890, filed Feb. 28, 2014, claiming priority based on Japanese Patent Application No. 2013-041105, filed Mar. 1, 2013, the contents of all of which are incorporated herein by reference in their entirety.

TECHNICAL FIELD

The present invention relates to a suspension for oral administration (in particular, a syrup) comprising amorphous tolvaptan, and a method for producing the same.

BACKGROUND ART

Tolvaptan, which is 7-chloro-5-hydroxy-1-[2-methyl-4-(2-methylbenzoylamino)benzoyl]-2,3,4,5-tetrahydro-1H-benzazepine, represented by Formula (I), is a vasopressin antagonist with aquaretic activity (Patent Literature 1). Tolvaptan is sold as a therapeutic agent against hyponatremia, body fluid retention in heart failure, and body fluid retention in liver cirrhosis.

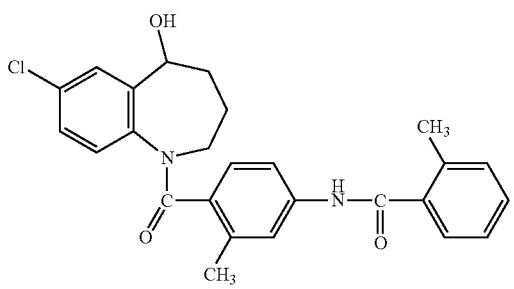

(I)

When tolvaptan is formulated into a solid formulation by using a common formulation technique, it becomes crystalline, resulting in reduced solubility and absorbability from the gastrointestinal tract. As a means for solving this problem, Patent Literature 2 reports that a composition comprising amorphous tolvaptan can be prepared by dissolving tolvaptan and hydroxypropyl cellulose in an organic solvent and spray-drying the mixture to obtain a powder, thereby improving solubility and absorbability from the gastrointestinal tract.

Examples of reports relating to the above formulation comprising amorphous tolvaptan include the following. For example, Patent Literature 3 reports that a pharmaceutical solid formulation with superior disintegration properties can be obtained by mixing a composition containing amorphous tolvaptan with specific low-substituted hydroxypropyl cellulose.

Patent Literature 4 reports that a matrix-type solid formulation with advanced release controllability can be obtained by mixing a composition containing amorphous tolvaptan with an enteric polymer and a specific sugar and/or sugar alcohol.

Patent Literature 5 reports that a gradual disintegration-type, sustained-release pharmaceutical solid formulation whose pharmacologically active substance-release behavior is controlled can be obtained by mixing a composition containing amorphous tolvaptan with calcium polycarbophil and a sugar and/or sugar alcohol.

CITATION LIST

Patent Literature

PTL 1: JP H04-154765A
PTL 2: JP H11-21241A (JP4210355B)
PTL 3: WO2008/156217 pamphlet (JP2010-530355A)
PTL 4: WO2009/051022 pamphlet (JP2011-500511A)
PTL 5: WO2010/026971 pamphlet (JP2012-501960A)

SUMMARY OF INVENTION

Technical Problem

The solid formulations disclosed in Patent Literature 2 to 5 described above, which comprise a composition containing amorphous tolvaptan, have excellent solubility of tolvaptan and excellent absorbability of tolvaptan from the gastrointestinal tract. Amorphous tolvaptan in the solid formulations remains stable without crystallizing, even after long-term storage.

The present inventors conducted research on a suspension for oral administration (e.g., a syrup) comprising a composition (powder or particle composition) containing amorphous tolvaptan, the suspension for oral administration being different from the above-described solid formulations for oral administration disclosed in Patent Literature 2 to 5. As a result, the present inventors independently confirmed that amorphous tolvaptan rapidly crystallizes in the suspension over time, resulting in significant reduction in solubility of tolvaptan and absorbability of tolvaptan from the gastrointestinal tract. There is thus a strong demand for a suspension for oral administration that can inhibit crystallization of amorphous tolvaptan in the suspension for a long period of time.

Accordingly, an object of the present invention is to provide a suspension for oral administration comprising amorphous tolvaptan that can inhibit crystallization of amorphous tolvaptan over time in the suspension, and stably maintain high solubility of tolvaptan and excellent absorbability of tolvaptan from the gastrointestinal tract.

Solution to Problem

To achieve the above objects, the present inventors conducted extensive research on techniques for inhibiting or delaying crystallization of amorphous tolvaptan over time in a suspension for oral administration comprising amorphous tolvaptan.

As a result, the present inventors found that crystallization of amorphous tolvaptan over time can be significantly inhibited or delayed by containing hydroxypropyl methylcellulose (hereafter may be referred to as "HPMC") in an aqueous suspension of particles containing amorphous tolvaptan. More specifically, the present inventors found that crystallization of amorphous tolvaptan can be significantly inhibited or delayed by setting the amount of HPMC in the aqueous suspension to 0.1 to 25% by weight based on the total weight of the aqueous suspension. The present inventors conducted further research based on the above findings, and accomplished the present invention.

The present invention provides the following suspension for oral administration, and method for producing the same.

Item 1. A suspension for oral administration, comprising:
   (a) particles containing amorphous tolvaptan;
   (b) hydroxypropyl methylcellulose (HPMC); and
   (c) a solvent.

Item 2. The suspension for oral administration according to item 1, wherein the amount of the HPMC (b) is 0.1 to 25% by weight based on the total weight of the suspension for oral administration.

Item 3. The suspension for oral administration according to item 1 or 2, wherein the HPMC (b) has a viscosity of 1 to 4000 mPa·s, preferably 1 to 500 mPa·s, more preferably 1 to 100 mPa·s, still more preferably 2 to 50 mPa·s, and particularly preferably 2 to 20 mPa·s in a 2% aqueous solution at 20° C.

Item 4. The suspension for oral administration according to any one of items 1 to 3, wherein the amount of the particles containing amorphous tolvaptan (a) is 0.01 to 5% by weight based on the total weight of the suspension for oral administration.

Item 5. The suspension for oral administration according to any one of items 1 to 4, wherein the particles containing amorphous tolvaptan (a) contain amorphous tolvaptan and optionally a polymer.

Item 6. The suspension for oral administration according to item 5, wherein the polymer is at least one member selected from the group consisting of hydroxypropyl cellulose (HPC) and hydroxypropyl methylcellulose (HPMC); preferably hydroxypropyl methylcellulose (HPMC).

Item 7. The suspension for oral administration according to item 5 or 6, wherein the weight ratio of the tolvaptan to the polymer in the particles containing amorphous tolvaptan (a) is 1:0 to 1:4 (preferably 4:1 to 1:2).

Item 8. The suspension for oral administration according to any one of items 1 to 7, wherein the solvent (c) is water.

Item 9. The suspension for oral administration according to any one of items 1 to 8, further comprising (d) a suspending agent and/or (e) a sweetener.

Item 10. The suspension for oral administration according to item 9, wherein the suspending agent (d) is at least one member selected from the group consisting of xanthan gum, gellan gum, carrageenan, carboxyvinyl polymers, and sodium carboxymethyl cellulose; preferably xanthan gum.

Item 11. The suspension for oral administration according to item 9 or 10, wherein the sweetener (e) is at least one member selected from the group consisting of mannitol, sorbitol, xylitol, maltitol, erythritol, sucrose, sucralose, aspartame, acesulfame potassium, saccharin, thaumatin, stevia extracts, trehalose, lactose, maltose, glucose, and glycerin; preferably at least one member selected from the group consisting of sorbitol, xylitol, and sucralose.

Item 12. The suspension for oral administration according to any one of items 1 to 11, further comprising at least one member selected from the group consisting of pH-adjusting agents, preservatives, stabilizers, and flavoring agents.

Item 13. The suspension for oral administration according to any one of items 1 to 12, which is in the form of a syrup (in particular, a syrup for pediatric use).

Item 14. A method for producing a suspension for oral administration, the method comprising uniformly dispersing (suspending) particles containing amorphous tolvaptan in an aqueous suspension containing HPMC or an aqueous solution containing HPMC.

Item 15. The method according to item 14, wherein the amount of the HPMC is 0.1 to 25% by weight based on the total weight of the suspension for oral administration.

Item 16. The suspension for oral administration according to items 1 to 13, for use as a drug for preventing, reducing, or treating hyponatremia, polycystic kidney disease, body fluid retention in heart failure, or body fluid retention in liver cirrhosis.

Item 17. Use of the suspension for oral administration according to items 1 to 13 for the production of a drug for preventing, reducing, or treating hyponatremia, polycystic kidney disease, body fluid retention in heart failure, or body fluid retention in liver cirrhosis.

Item 18. Use of a suspension comprising (a) particles containing amorphous tolvaptan, (b) hydroxypropyl methylcellulose (HPMC), and (c) a solvent for the production of a drug for preventing, reducing, or treating hyponatremia, polycystic kidney disease, body fluid retention in heart failure, or body fluid retention in liver cirrhosis.

Item 19. A method for preventing, reducing, or treating hyponatremia, polycystic kidney disease, body fluid retention in heart failure, or body fluid retention in liver cirrhosis, the method comprising administering the suspension for oral administration according to items 1 to 13 to a patient (subject) in recognized need of prevention, reduction, or treatment of hyponatremia, polycystic kidney disease, body fluid retention in heart failure, or body fluid retention in liver cirrhosis.

Item 20. The suspension for oral administration according to any one of items 1 to 13, wherein the suspension for oral administration comprising:
   (a) particles containing amorphous tolvaptan: 0.01 to 5% by weight (preferably 0.02 to 2% by weight, more preferably 0.05 to 1% by weight, and particularly preferably 0.05 to 0.5% by weight),
   (b) hydroxypropyl methylcellulose (HPMC): 0.1 to 25% by weight (preferably 0.1 to 10% by weight, more preferably 0.1 to 5% by weight, still more preferably 0.1 to 4% by weight, and particularly preferably 0.1 to 3% by weight),
   (c) a solvent: 20 to 99% by weight (preferably 20 to 80% by weight, more preferably 30 to 70% by weight, still more preferably 40 to 65% by weight, further more preferably 40 to 60% by weight, and particularly preferably 45 to 60% by weight),
   (d) a suspending agent: 0 to 5% by weight (preferably 0.05 to 2% by weight, more preferably 0.1 to 2% by weight, still more preferably 0.1 to 1% by weight, and particularly preferably 0.3 to 0.8% by weight),
   (e) a sweetener: 0 to 70% by weight (preferably 10 to 60% by weight, more preferably 20 to 60% by weight, and particularly preferably 30 to 50% by weight), and
   (f) one or more other pharmaceutically acceptable components: 0 to 5% by weight (preferably 0.01 to 5% by weight, more preferably 0.02 to 1% by weight, and particularly preferably 0.02 to 0.5% by weight) of each component,
   based on the total weight of the suspension for oral administration.

Item 21. The suspension for oral administration according to any one of items 1 to 13, wherein the suspension for oral administration comprising:
   (a) particles containing amorphous tolvaptan: 0.01 to 5% by weight (preferably 0.02 to 2% by weight, more preferably 0.05 to 1% by weight, and particularly preferably 0.05 to 0.5% by weight),
   (b) hydroxypropyl methylcellulose (HPMC): 0.1 to 25% by weight (preferably 0.2 to 10% by weight, more preferably 0.3 to 5% by weight, still more preferably 0.5 to 5% by weight, and particularly preferably 0.5 to 4% by weight),
   (c) a solvent: 20 to 99% by weight (preferably 20 to 80% by weight, more preferably 30 to 70% by weight, still more preferably 40 to 65% by weight, further more preferably 40 to 60% by weight, and particularly preferably 45 to 60% by weight), (d) a suspending agent: 0 to 5% by weight (preferably 0.05 to 2% by weight, more preferably 0.1 to 2% by weight, still more preferably 0.1 to 1% by weight, and particularly preferably 0.3 to 0.8% by weight), (e) a sweetener: 0 to 70% by weight (preferably 10 to 60% by weight, more preferably 20 to 60% by weight, and particularly preferably 30 to 50% by weight), and (f) one or more other pharmaceutically acceptable components: 0 to 5% by weight (preferably 0.01 to 5% by weight, more preferably 0.02 to 1% by weight, and particularly preferably 0.02 to 0.5% by weight) of each component, based on the total weight of the suspension for oral administration.

Advantageous Effects of Invention

The suspension for oral administration of the present invention (e.g., a syrup) can inhibit or delay crystallization of amorphous tolvaptan over time in the suspension, and stably maintain high solubility of tolvaptan and excellent absorbability of tolvaptan from the gastrointestinal tract.

By further adding a suspending agent (thickener) to the suspension for oral administration of the present invention, crystallization of amorphous tolvaptan can be further inhibited or delayed, and particles containing amorphous tolvaptan can be uniformly dispersed in the suspension and stably maintained.

The patent or application file contains at least one drawing executed in color. Copies of this patent or patent application publication with color drawings will be provided by the Office upon request and payment of the necessary fee.

BRIEF DESCRIPTION OF DRAWINGS

FIG. 1 illustrates dissolution profiles after each of the formulations (Preparation Examples 1A to 1D) was stored at 40° C. for 4 weeks in Test Example 1.

FIG. 2 is polarizing microscope photographs (×100) after each of the formulations (Preparation Examples 1C and 1D) was stored at 40° C. for 4 weeks in Test Example 1.

FIG. 3-1 illustrates dissolution profiles immediately after production of each of the formulations (Preparation Examples 2A to 2D) in Test Example 2.

FIG. 3-2 illustrates dissolution profiles of the formulations (Preparation Examples 2A to 2D) after storage at 4° C.-40° C. cycle/day for 8 weeks in Test Example 2.

FIG. 4 is polarizing microscope photographs (×100) after each of the formulations (Preparation Examples 2A and 2B) was stored at 4° C.-40° C. cycle/day for 8 weeks in Test Example 2.

FIG. 5 illustrates dissolution profiles of the formulation (Preparation Example 3A) immediately after production and after storage at 4° C.-40° C. cycle/day for 8 weeks and 12 weeks in Test Example 3.

FIG. 6 is a polarizing microscope photograph (×100) after the formulation (Preparation Example 3A) was stored at 4° C.-40° C. cycle/day for 12 weeks in Test Example 3.

FIG. 7 illustrates dissolution profiles of the formulation (Preparation Example 4A) immediately after production and after storage at 40° C. for 4 weeks and 8 weeks in Test Example 4.

FIG. 8 illustrates dissolution profiles of the formulation (Preparation Example 4B) immediately after production and after storage at 40° C. for 4 weeks and 8 weeks in Test Example 4.

FIG. 9 illustrates dissolution profiles of the formulations (Preparation Examples 5B to 5D), using the tablet (Preparation Example 5A) as a control in Test Example 5.

FIG. 10 illustrates PK profiles of the formulations (Preparation Examples 5B to 5D), using the tablet (Preparation Example 5A) as a control in Test Example 5.

FIG. 11 illustrates dissolution profiles of the formulations (Preparation Example 6A) immediately after production and after storage at 5° C. for 1 week and 2 weeks in Test Example 6.

FIGS. 12(a) and 12(b) illustrate the appearance and tolvaptan content at each portion of each of the formulations (Preparation Examples 6I and 6R) immediately after production and after storage at 5° C. for 3 days in Test Example 6.

DESCRIPTION OF EMBODIMENTS

1. Suspension for Oral Administration

The suspension for oral administration of the present invention comprises (a) particles containing amorphous tolvaptan, (b) hydroxypropyl methylcellulose (HPMC), and (c) a solvent. More specifically, the suspension for oral administration of the present invention is a liquid formulation in which (b) HPMC is dissolved or suspended in a solvent and in which particles containing amorphous tolvaptan are suspended in the solvent. By setting the amount of (b) HPMC to 0.1 to 25% by weight based on the total weight of the suspension for oral administration, crystallization of amorphous tolvaptan can be inhibited or delayed.

(a) Particles Containing Amorphous Tolvaptan

Tolvaptan is a compound represented by Formula (I) described above, and contains an asymmetric carbon atom (hydroxy-bonded carbon atom). The term "tolvaptan" encompasses a racemic mixture, optically active substances (R-(+) form and S-(−) form), and a mixture of the optically active substances. Tolvaptan is preferably racemic tolvaptan. Tolvaptan can be produced by a known method. For example, tolvaptan can be produced according to the method disclosed in JP H04-154765A (Patent Literature 1).

Tolvaptan encompasses anhydrides, solvates (e.g., hydrates, alcoholates, etc.), co-crystals, etc., of tolvaptan. Further, tolvaptan encompasses those in which one or more atoms in the tolvaptan molecule are replaced by one or more isotopic atoms. Examples of isotopic atoms include deuterium ($^2$H), tritium ($^3$H), $^{13}$C, $^{14}$N, $^{18}$O, and the like.

The term "amorphous" in amorphous tolvaptan indicates that the content of crystalline tolvaptan based on total tolvaptan content of the particles is less than 5% by weight, preferably less than 3% by weight, more preferably less than 1% by weight, and particularly preferably indicates that no crystalline tolvaptan is detected. The content of crystalline tolvaptan based on total tolvaptan content of the particles can be determined by measuring X-ray diffraction of the particles.

The term "particles containing amorphous tolvaptan" encompasses particles consisting essentially of amorphous tolvaptan, and particles containing amorphous tolvaptan and a polymer component (particles of solid dispersion). Examples of the polymer component include water-soluble polymers, enteric polymers, gastrosoluble polymers, water-insoluble polymers, biodegradable polymers, and the like. Specific examples of the polymer component include polyvinylpyrrolidone (PVP), hydroxypropyl cellulose (HPC), hydroxypropyl methylcellulose phthalate (HPMCP), hydroxypropyl methylcellulose (HPMC), methylcellulose (MC), povidone, crospovidone, copolyvidone, polyvinyl caprolactam-polyvinyl acetate-polyethylene glycol graft copolymers, methacrylic acid copolymer L, methacrylic acid copolymers, ethyl cellulose, cellulose acetate, aminoalkyl copolymer RS (e.g., trade name, Eudragit RS or RL), ethyl acrylate/methyl methacrylate copolymers (e.g., Eudragit NE 30 D), and the like. They may be used singly, or in a combination of two or more. Preferable examples of the polymer component include HPC and HPMC, and HPMC is more preferable.

The weight ratio of tolvaptan to polymer component in the particles is generally 1:0 to 1:4, preferably 8:1 to 1:4, more preferably 4:1 to 1:2, still more preferably 2:1 to 2:3, and particularly preferably 2:1 to 1:1.

The particles containing amorphous tolvaptan can be prepared by a variety of methods.

For example, the particles containing amorphous tolvaptan can be prepared by a spray-drying method in accordance with the disclosure of JP H11-21241A (Patent Literature 2). More specifically, the particles containing amorphous tolvaptan can be prepared by dissolving tolvaptan together with, if necessary, a polymer component in an organic solvent that can dissolve tolvaptan and the polymer component; evaporating the organic solvent; and forming the residue into powder (particles). Examples of the polymer component include water-soluble polymers, biodegradable polymers, and the like. Examples of organic solvents include methylene chloride, mixed solution of methylene chloride and ethanol, mixed solution of methylene chloride and methanol, and the like. By spray-drying the obtained solution, a powder (particles) with a preferable particle size distribution can be obtained. Further, the residual solvent can be removed by drying the obtained powder under reduced pressure or freeze-drying the obtained powder, if necessary.

When a spray-drying method is used, the mean particle size of the particles containing amorphous tolvaptan can be controlled by adjusting the type of a spray nozzle, the tolvaptan concentration and polymer concentration in an organic solvent, spray rate, etc.

The mean particle size of the particles is generally about 0.1 to about 200 μm, preferably about 1 to about 150 μm, and more preferably about 10 to about 100 μm. The absorption rate of tolvaptan can be controlled by controlling the mean particle size of the particles. The mean particle size of the particles is a volume mean diameter, and can be determined using a laser diffraction particle size distribution meter.

The amount of particles containing amorphous tolvaptan in the suspension for oral administration is generally 0.01 to 5% by weight, preferably 0.02 to 2% by weight, more preferably 0.05 to 1% by weight, and particularly preferably 0.05 to 0.5% by weight, based on the total weight of the suspension for oral administration.

The amount of tolvaptan in the suspension for oral administration is generally 0.01 to 5% by weight, preferably 0.02 to 2% by weight, more preferably 0.05 to 1% by weight, and particularly preferably 0.05 to 0.5% by weight, based on the total weight of the suspension for oral administration.

(b) Hydroxypropyl Methylcellulose (HPMC)

HPMC is a water-soluble cellulose ether in which 2-hydroxypropyl is introduced into methylcellulose (MC) described in the Specifications and Standards for Food Additives, and corresponds to hypromellose described in the Japanese Pharmacopoeia. Examples of HPMC include HPMC substitution types 2910, 2906, and 2208; and the like. HPMC is preferably substitution type 2910. Further, HPMC has a viscosity of generally 1 to 4000 mPa·s, preferably 1 to 500 mPa·s, more preferably 1 to 100 mPa·s, still more preferably 2 to 50 mPa·s, and particularly preferably 2 to 20 mPa·s in a 2% aqueous solution at 20° C.

Known HPMC may be used. Specific examples thereof include TC-5E, TC-5M, TC-5R, TC-5S, 60SH, 65SH (all produced by Shin-Etsu Chemical Co., Ltd.), and the like.

The amount of HPMC in the suspension for oral administration is generally 0.1 to 25% by weight, preferably 0.1 to 10% by weight, more preferably 0.1 to 5% by weight, still more preferably 0.1 to 4% by weight, and particularly preferably 0.1 to 3% by weight.

In another embodiment, the amount of HPMC in the suspension for oral administration is 0.1 to 25% by weight, preferably 0.2 to 10% by weight, more preferably 0.3 to 5% by weight, still more preferably 0.5 to 5% by weight, and particularly preferably 0.5 to 4% by weight, based on the total weight of the suspension for oral administration.

The amount of HPMC in the suspension for oral administration is generally 0.1 to 30 parts by weight, preferably 0.1 to 25 parts by weight, more preferably 0.5 to 10 parts by weight, and particularly preferably 3 to 8 parts by weight, relative to 1 part by weight of the particles containing amorphous tolvaptan.

When the suspension for oral administration of the present invention comprises HPMC in the above ranges, crystallization of amorphous tolvaptan can be inhibited or delayed, thereby stably maintaining high solubility of tolvaptan and excellent absorbability of tolvaptan from the gastrointestinal tract.

(c) Solvent

Any solvent is usable as a solvent (or liquid medium) used in the suspension for oral administration of the present invention, as long as it is a pharmaceutically acceptable solvent. The solvent is generally water (purified water).

The amount of solvent in the suspension for oral administration can be suitably adjusted according to the amounts of other components. For example, the amount of solvent is generally 20 to 99% by weight, preferably 20 to 80% by weight, more preferably 30 to 70% by weight, still more preferably 40 to 65% by weight, further more preferably 40 to 60% by weight, and particularly preferably 45 to 60% by weight, based on the total weight of the suspension for oral administration.

(d) Suspending Agent

The suspension for oral administration of the present invention may further comprise (d) a suspending agent.

There is no particular limitation to the suspending agent, as long as the suspending agent can suspend particles containing amorphous tolvaptan in a solvent. Examples of the suspending agent include thickeners, such as xanthan gum, gellan gum, carrageenan, carboxyvinyl polymers, and sodium carboxymethyl cellulose. They may be used singly, or in a combination of two or more. In particular, xanthan gum and gellan gum are preferable, and xanthan gum is more preferable.

The amount of suspending agent is generally 0 to 5% by weight, preferably 0.05 to 2% by weight, more preferably 0.1 to 2% by weight, still more preferably 0.1 to 1% by weight, and particularly preferably 0.3 to 0.8% by weight, based on the total weight of the suspension for oral administration.

Adding suspending agent (d) (in particular, thickener) to the suspension for oral administration of the present invention allows crystallization of amorphous tolvaptan to be further inhibited or delayed. Further, the particles containing amorphous tolvaptan can be uniformly dispersed, and the dispersion can be maintained (improvement in suspension stability). More specifically, even after the suspension for oral administration is allowed to stand for a long period of time, the dispersion of the suspension for oral administration can be maintained. This enables uniform distribution of the particles containing amorphous tolvaptan in the suspension for oral administration to be maintained without dispersing (e.g., shaking) the suspension for oral administration again. Accordingly, a predetermined amount of tolvaptan can be weighed and administered in a simple manner by measuring the suspension for oral administration on a volume basis.

(e) Sweetener

The suspension for oral administration of the present invention may further comprise (e) a sweetener.

Examples of the sweetener include a sugar and/or a sugar alcohol. Specific examples of the sweetener include mannitol, sorbitol, xylitol, maltitol, erythritol, sucrose, sucralose, aspartame, acesulfame potassium, saccharin, thaumatin, stevia extracts, trehalose, lactose, maltose, glucose, glycerin, and the like. They may be used singly, or in a combination of two or more. Among them, sorbitol, xylitol, sucrose, and sucralose are preferable; and sorbitol, xylitol, and sucralose are more preferable. Examples of the combination of two or more sweetners include a combination of sorbitol and sucralose; a combination of xylitol and sucralose; a combination of sorbitol and xylitol; a combination of sorbitol, sucralose and xylitol; and the like.

The amount of sweetener is generally 0 to 70% by weight, preferably 10 to 60% by weight, more preferably 20 to 60% by weight, and particularly preferably 30 to 50% by weight, based on the total weight of the suspension for oral administration.

(f) Other Components

The suspension for oral administration of the present invention may further comprise (f) one or more other pharmaceutically acceptable components, such as a pH-adjusting agent, a preservative, a stabilizer, and a flavoring agent, if necessary.

The amount of each of the other components is generally 0 to 5% by weight, preferably 0.01 to 5% by weight, more preferably 0.02 to 1% by weight, and particularly preferably 0.02 to 0.5% by weight, based on the total weight of the suspension for oral administration.

The pH-adjusting agent may be used in an amount sufficient to adjust the pH of the suspension to a range of about 3 to about 4, and preferably 3.2 to 3.8. To adjust the pH to the desired pH, either a base or acid may be used. When the pH must be lowered, an acidic pH-adjusting agent (e.g., hydrochloric acid, phosphoric acid, acetic acid, citric acid, tartaric acid, and the like; preferably citric acid hydrate) may be used. When the pH must be raised, a basic pH-adjusting agent (e.g., sodium hydroxide, potassium hydroxide, calcium carbonate, magnesium oxide, magnesium hydroxide, and the like; preferably sodium hydroxide) may be used.

Examples of the preservative include benzoic acid; sodium benzoate; quaternary ammonium salts, such as benzalkonium chloride, and benzethonium chloride; cationic compounds, such as chlorhexidine gluconate; p-hydroxybenzoates, such as methyl p-hydroxybenzoate, ethyl p-hydroxybenzoate, and propyl p-hydroxybenzoate; alcohol compounds, such as chlorobutanol and benzyl alcohol; sodium dehydroacetate; thimerosal; and the like. Sodium benzoate is preferable.

Examples of the stabilizer include sodium edetate (EDTA-Na), and the like.

Examples of the flavoring agent include cherry flavor, and the like.

Preferable Embodiment of the Suspension for Oral Administration

A preferable embodiment of the suspension for oral administration of the present invention is, for example, a suspension for oral administration that comprises (a) particles containing amorphous tolvaptan: 0.01 to 5% by weight (preferably 0.02 to 2% by weight, more preferably 0.05 to 1% by weight, and particularly preferably 0.05 to 0.5% by weight), (b) HPMC: 0.1 to 25% by weight (preferably 0.1 to 10% by weight, more preferably 0.1 to 5% by weight, more preferably 0.1 to 4% by weight, and particularly preferably 0.1 to 3% by weight; or in another embodiment, 0.1 to 25% by weight, preferably 0.2 to 10% by weight, more preferably 0.3 to 5% by weight, still more preferably 0.5 to 5% by weight, and particularly preferably 0.5 to 4% by weight), (c) a solvent: 20 to 99% by weight (preferably 20 to 80% by weight, more preferably 30 to 70% by weight, still more preferably 40 to 65% by weight, further more preferably 40 to 60% by weight, and particularly preferably 45 to 60% by weight), (d) a suspending agent: 0 to 5% by weight (preferably 0.05 to 2% by weight, more preferably 0.1 to 2% by weight, still more preferably 0.1 to 1% by weight, and particularly preferably 0.3 to 0.8% by weight), (e) a sweetener: 0 to 70% by weight (preferably 10 to 60% by weight, more preferably 20 to 60% by weight, and particularly preferably 30 to 50% by weight), and (f) one or more other pharmaceutically acceptable components: 0 to 5% by weight (preferably 0.01 to 5% by weight, more preferably 0.02 to 1% by weight, and particularly preferably 0.02 to 0.5% by weight) of each component, based on the total weight of the suspension for oral administration.

Alternatively, the amount of each component in the suspension for oral administration can be expressed as follows. For example, a formulation comprising:

relative to 1 part by weight of (a) particles comprising amorphous tolvaptan, (b) HPMC: 0.1 to 30 parts by weight (preferably 0.1 to 25 parts by weight, more preferably 0.5 to 10 parts by weight), (c) a solvent: 100 to 1000 parts by weight (preferably 100 to 600 parts by weight, and more preferably 200 to 500 parts by weight), (d) a suspending agent: 0 to 50 parts by weight (preferably 0 to 10 parts by weight, and more preferably 1 to 5 parts by weight), (e) a sweetener: 0 to 500 parts by weight (preferably 100 to 400 parts by weight), and (f) one or more other pharmaceutically acceptable components: 0 to 40 parts by weight (preferably 0 to 10 parts by weight, more preferably 0.1 to 3 parts by weight) of each component, can be mentioned.

Method for Producing the Suspension for Oral Administration

The suspension for oral administration of the present invention can be prepared by mixing the above-described components, i.e., (a) particles containing amorphous tolvaptan, (b) HPMC, and (c) a solvent together with, if necessary (d) a suspending agent, (e) a sweetener, and/or (f) one or more other pharmaceutically acceptable components. A uniform suspension can be prepared by using a known mixing method, such as stirring, shaking, and ultrasonic irradiation, after the components are added.

Preferable examples of the preparation method include a method in which particles containing amorphous tolvaptan are uniformly dispersed (suspended) in an aqueous suspension containing hydroxypropyl methylcellulose (HPMC) or an aqueous solution containing HPMC.

Specific examples of the method include a method in which HPMC is added to purified water together with, if necessary, a sweetener, a suspending agent, a preservative, a stabilizer, and/or a flavoring agent to prepare an aqueous suspension or an aqueous solution, and particles containing amorphous tolvaptan are added thereto and uniformly dispersed (suspended).

More specifically, for example, the following method can be mentioned: the method comprises the steps of:

(1) dispersing a sweetener and a suspending agent in purified water, stirring the mixture at 79 to 85° C. for 0.5 to 3 hours to obtain a uniform solution, and then cooling the solution to 27 to 33° C.;

(2) individually adding and dissolving a preservative and a stabilizer in purified water;

(3) individually adding and dissolving hydroxypropyl methylcellulose (HPMC) and a pH-adjusting agent in purified water;

(4) adding the solution of (2), the solution of (3), and a flavoring agent to the solution of (1), and cooling the mixture to 4 to 10° C. with stirring for 0.5 to 3 hours; and (5) adding particles containing amorphous tolvaptan to the aqueous suspension or aqueous solution obtained in (4), stirring the mixture at 4 to 10° C. for 0.5 to 3 hours, and uniformly dispersing the particles.

The amount of each component can be adjusted such that the amount of each component in the final suspension is within the above-described ranges.

The pH of the suspension for oral administration after preparation is generally about 3 to about 4, and preferably 3.2 to 3.8.

The suspension for oral administration of the present invention comprises (a) particles containing amorphous tolvaptan, (b) hydroxypropyl methylcellulose (HPMC), and (c) a solvent.

Dispersion (suspension) of the particles in the solvent containing HPMC enables crystallization of amorphous tolvaptan to be inhibited or delayed. In addition, crystallization of amorphous tolvaptan can be further inhibited or delayed by setting the amount of HPMC to 0.1 to 25% by weight based on the total weight of the suspension for oral administration. As a result, high solubility of tolvaptan and excellent absorbability of tolvaptan from the gastrointestinal tract can be stably maintained.

Further, in addition to the inhibition of crystallization, adding a suspending agent (thickener) enables the particles containing amorphous tolvaptan to be uniformly dispersed in the suspension, and enables the dispersion to be stably maintained.

The suspension for oral administration of the present invention can be generally used as a syrup, in particular a syrup for pediatric use.

The suspension for oral administration of the present invention can be prepared by formulating a solid formulation for oral administration (e.g., a dry syrup) into the above-described suspension for oral administration at the time of use.

2. Administration Method

The formulation of the present invention relates to a suspension for oral administration (in particular, a syrup) and a solid formulation for oral administration (in particular, a dry syrup, etc.). The suspension for oral administration can be orally administered to a human. A solid formulation for oral administration is suspended at the time of use in a solvent (e.g., water) to prepare the suspension for oral administration of the present invention, and the suspension can be orally administered to a human.

The formulation of the present invention can efficiently exhibit the vasopressin antagonism of tolvaptan. Thus, hyponatremia, polycystic kidney, body fluid retention caused by heart failure, or body fluid retention caused by liver cirrhosis can be prevented, reduced, or treated by orally administering the formulation to a patient (sample) who requires prevention, reduction, or treatment of hyponatremia, polycystic kidney, body fluid retention caused by heart failure, body fluid retention caused by liver cirrhosis, etc. Thus, the formulation can be used as a drug for preventing, reducing, or treating hyponatremia, polycystic kidney, body fluid retention caused by heart failure, or body fluid retention caused by liver cirrhosis.

The dosage of the suspension for oral administration of the present invention is suitably selected according to the dosage regimen, the patient's age and sex, the severity of the disease, and other conditions. Tolvaptan is generally orally administered in an amount of 0.001 to 100 mg/kg (body weight)/day, preferably 0.01 to 10 mg/kg (body weight)/day in one or more oral administrations.

Since the dosage varies depending on various conditions, a dosage lower than the above range may be sufficient, and a dosage higher than the above range may be required.

The formulation of the present invention can be used in the form of syrup, dry syrup, etc., particularly preferably in the form of syrup or dry syrup for children.

EXAMPLES

Next, the present invention is specifically explained using Examples; however, the present invention is not limited thereto or thereby.

Test Example 1

Dissolution Test of Formulation

Preparation Example 1A

Suspension: Purified Water Alone

Particles (0.15 g) (spray-dried product; tolvaptan SD (spray-dried) powder) containing amorphous tolvaptan including tolvaptan and hydroxypropyl cellulose (HPC; HPC-SL, produced by Nippon Soda Co., Ltd., the same as below) in a weight ratio of 2:1 were added to purified water (100 g), and dispersed by stirring well.

Preparation Example 1B

Suspension: 20% Xylitol

Xylitol (20 g) was added to purified water (80 g), and dissolved by stirring well. Particles (0.15 g) (spray-dried product; tolvaptan SD powder) containing amorphous tolvaptan including tolvaptan and hydroxypropyl cellulose (HPC; HPC-SL) in a weight ratio of 2:1 were added thereto, and dispersed by stirring well.

Preparation Example 1C

Suspension: 5% HPC

Hydroxypropyl cellulose (5 g) (HPC; HPC-SL) was added to purified water (95 g), and dissolved by stirring well.

Particles (0.15 g) (spray-dried product; tolvaptan SD powder) containing amorphous tolvaptan including tolvaptan and hydroxypropyl cellulose (HPC; HPC-SL) in a weight ratio of 2:1 were added thereto, and dispersed by stirring well.

Preparation Example 1D

Suspension: 5% HPMC

Hydroxypropylmethyl cellulose (5 g) (HPMC; hypromellose 2910 produced by Shin-Etsu Chemical Co., Ltd.) was added to water (95 g), and dissolved by stirring well. Amorphous tolvaptan (0.15 g) (spray-dried product; tolvaptan SD powder) containing tolvaptan and hydroxypropyl cellulose (HPC; HPC-SL) in a weight ratio of 2:1 was added thereto, and dispersed by stirring well.

The thus-prepared formulations of Preparation Examples 1A to 1D were stored at 40° C. for 4 weeks, and a dissolution test was performed according to the second method (paddle method) of the Japanese Pharmacopoeia dissolution test. FIG. 1 shows the results.
Dissolution Medium: 0.22% Sodium lauryl sulfate (SLS) aqueous solution, 900 ml
Measurement method: Difference of absorbance at a wavelength of 268 nm and at a wavelength of 350 nm
Paddle rotation speed: 50 rpm
Number of samples: n=1

Polarization microscope photographs (×100) of the formulations of Preparation Examples 1C and 1D after storage were taken. FIG. 2 shows the results.

FIG. 1 indicates that only the suspension containing HPMC of Preparation Example 1D showed no reduction in dissolution rate after storage at 40° C. for 4 weeks. FIG. 2 indicates that a large amount of crystal tolvaptan was observed in the suspension of Preparation Example 1C after storage; however, no crystal tolvaptan was observed in the suspension of Preparation Example 1D. This reveals that the addition of HPMC to the suspension can suppress the crystallization of amorphous tolvaptan.

Test Example 2

Dissolution Test of Formulation

Preparation Example 2A

Suspension: No HPMC Addition

Xylitol (80 g) and gellan gum (0.2 g) were added to purified water (79.5 g), and dissolved by stirring well (Solution A). Separately, sodium benzoate (0.4 g) and sodium edetate (EDTA-Na) (0.02 g) were added to water (9.58 g), and dissolved by stirring well (Solution B). Separately, citric acid hydrate (0.6 g) was added to water (29.4 g), and dissolved by stirring well (Solution C). After adding Solution B and Solution C to Solution A, and stirring the mixture well, particles (0.3 g) (spray-dried product; tolvaptan SD powder) containing amorphous tolvaptan including tolvaptan and hydroxypropyl cellulose (HPC; HPC-SL) in a weight ratio of 2:1 were added thereto, and dispersed by stirring well.

Preparation Example 2B

Suspension: 0.1% HPMC

Xylitol (80 g) and gellan gum (0.2 g) were added to purified water (79.5 g), and dissolved by stirring well (Solution A). Separately, sodium benzoate (0.4 g) and sodium edetate (EDTA-Na) (0.02 g) were added to water (9.58 g), and dissolved by stirring well (Solution B). Separately, hydroxypropylmethyl cellulose (0.2 g) (HPMC; hypromellose 2910) and citric acid hydrate (0.6 g) were added to water (29.2 g), and dissolved by stirring well (Solution C). After adding Solution B and Solution C to Solution A, and stirring the mixture well, particles (0.3 g) (spray-dried product; tolvaptan SD powder) containing amorphous tolvaptan including tolvaptan and hydroxypropyl cellulose (HPC; HPC-SL) in a weight ratio of 2:1 were added thereto, and dispersed by stirring well.

Preparation Example 2C

Suspension: 0.3% HPMC

Xylitol (80 g) and gellan gum (0.2 g) were added to purified water (79.5 g), and dissolved by stirring well (Solution A). Separately, sodium benzoate (0.4 g) and sodium edetate (EDTA-Na) (0.02 g) were added to water (9.58 g), and dissolved by stirring well (Solution B). Separately, hydroxypropylmethyl cellulose (0.6 g) (HPMC; hypromellose 2910) and citric acid hydrate (0.6 g) were added to water (28.8 g), and dissolved by stirring well (Solution C). After adding Solution B and Solution C to Solution A, and stirring the mixture well, particles (0.3 g) (spray-dried product; tolvaptan SD powder) containing amorphous tolvaptan including tolvaptan and hydroxypropyl cellulose (HPC; HPC-SL) in a weight ratio of 2:1 were added thereto, and dispersed by stirring well.

Preparation Example 2D

Suspension: 1.0% HPMC

Xylitol (80 g) and gellan gum (0.2 g) were added to purified water (79.5 g), and dissolved by stirring well (Solution A). Separately, sodium benzoate (0.4 g) and sodium edetate (EDTA-Na) (0.02 g) were added to water (9.58 g), and dissolved by stirring well (Solution B). Separately, hydroxypropylmethyl cellulose (2 g) (HPMC; hypromellose 2910) and citric acid hydrate (0.6 g) were added to water (27.4 g), and dissolved by stirring well (Solution C). After adding Solution B and Solution C to Solution A, and stirring the mixture well, particles (0.3 g) (spray-dried product; tolvaptan SD powder) containing amorphous tolvaptan including tolvaptan and hydroxypropyl cellulose (HPC; HPC-SL) in a weight ratio of 2:1 were added thereto, and dispersed by stirring well.

Table 1 shows the component composition of the formulations prepared in Preparation Examples 2A to 2D. All figures are expressed in wt %.

TABLE 1

| Component | Preparation Example 2A 0% HPMC | Preparation Example 2B 0.1% HPMC | Preparation Example 2C 0.3% HPMC | Preparation Example 2D 1.0% HPMC |
| --- | --- | --- | --- | --- |
| Tolvaptan SD powder | 0.15 | 0.15 | 0.15 | 0.15 |
| Xylitol | 40.00 | 40.00 | 40.00 | 40.00 |
| HPMC | 0.00 | 0.10 | 0.30 | 1.00 |
| Gellan gum | 0.10 | 0.10 | 0.10 | 0.10 |
| Sodium benzoate | 0.20 | 0.20 | 0.20 | 0.20 |

TABLE 1-continued

| Component | Preparation Example 2A 0% HPMC | Preparation Example 2B 0.1% HPMC | Preparation Example 2C 0.3% HPMC | Preparation Example 2D 1.0% HPMC |
|---|---|---|---|---|
| EDTA•2Na | 0.01 | 0.01 | 0.01 | 0.01 |
| Citric acid hydrate | 0.30 | 0.30 | 0.30 | 0.30 |
| Purified water | 59.24 | 59.14 | 58.94 | 58.24 |
| Total | 100.00 | 100.00 | 100.00 | 100.00 |

The thus-prepared formulations of Preparation Examples 2A to 2D were subjected to a dissolution test according to the second method (paddle method) of the Japanese Pharmacopoeia dissolution test, (i) immediately after preparation, and (ii) after 8 weeks of storage at a cycle of 4 to 40° C. each day (stored at 4° C. for 12 hours and 40° C. for 12 hours each day). The conditions of the dissolution test were the same as those in Test Example 1. (i) of FIG. 3-1 and (ii) of FIG. 3-2 show the results.

FIG. 3-1 and FIG. 3-2 indicate that a reduction in dissolution rate of amorphous tolvaptan was not observed in the suspensions (Preparation Examples 2B, 2C, and 2D) containing 0.1 to 1.0% HPMC, even after storage at a cycle of 4 to 40° C. each day for 8 weeks. In contrast, in the suspension (Preparation Example 2A) containing no HPMC, a reduction in dissolution rate was not observed immediately after production; however, a significant reduction in dissolution rate was observed after 8 weeks of storage.

Polarization microscope photographs (×100) of the formulations of Preparation Examples 2A and 2B after storage were taken. FIG. 4 shows the results.

FIG. 4 indicates that a large amount of crystal tolvaptan was observed in the suspension of Preparation Example 2A after storage; however, no crystal tolvaptan was observed in the suspension of Preparation Example 2B (the same applies to Preparation Examples 2C and 2D). This revealed that the addition of 0.1 to 1.0% HPMC to each suspension can suppress the crystallization of amorphous tolvaptan.

Test Example 3

Xanthan Gum Used in Place of Gellan Gum in Suspension

Preparation Example 3A

Suspension: 0.5% Xanthan Gum

Xylitol (80 g) and xanthan gum (1 g) were added to purified water (78.7 g), and dissolved by stirring well (Solution A). Separately, sodium benzoate (0.4 g) and sodium edetate (EDTA-Na) (0.1 g) were added to water (9.5 g), and dissolved by stirring well (Solution B). Separately, hydroxypropylmethyl cellulose (0.6 g) (HPMC; hypromellose 2910) and citric acid hydrate (0.6 g) were added to water (28.8 g), and dissolved by stirring well (Solution C). After adding Solution B and Solution C to Solution A, and stirring the mixture well, particles (0.3 g) (spray-dried product; tolvaptan SD powder) containing amorphous tolvaptan including tolvaptan and hydroxypropyl cellulose (HPC; HPC-SL) in a weight ratio of 2:1 were added thereto, and dispersed by stirring well.

Table 2 shows the component composition of the formulations prepared in Preparation Example 3A. All figures are expressed in wt %.

TABLE 2

| Component | Preparation Example 3A 0.5% xanthan gum |
|---|---|
| Tolvaptan SD powder | 0.15 |
| Xylitol | 40.0 |
| HPMC | 0.30 |
| Xanthan gum | 0.50 |
| Sodium benzoate | 0.20 |
| EDTA•2Na | 0.05 |
| Citric acid hydrate | 0.30 |
| Purified water | 58.5 |
| Total | 100.0 |

The thus-prepared formulation of Preparation Example 3A was subjected to a dissolution test according to the second method (paddle method) of the Japanese Pharmacopoeia dissolution test immediately after production, and after 8 weeks and 12 weeks of storage at a cycle of 4 to 40° C. each day. The conditions of the dissolution test were the same as those in Test Example 1. FIG. 5 shows the results.

FIG. 5 indicates that a reduction in dissolution rate of amorphous tolvaptan was not observed in the suspension (Preparation Example 3A) in which xanthan gum was used in place of gellan gum, even after storage at a cycle of 4 to 40° C. each day for 12 weeks.

A polarization microscope photograph (×100) of the formulation of Preparation Example 3A after storage was taken. FIG. 6 shows the results.

FIG. 6 indicates that crystal tolvaptan was not observed in the suspension of Preparation Example 3A after storage. This reveals that the crystallization of amorphous tolvaptan was suppressed in the suspension in which xanthan gum was used in place of gellan gum.

Test Example 4

Evaluation of HPMC and HPC in Particles

Preparation Example 4A

Suspension: HPC-SD

Xylitol (80 g), sucralose (0.4 g), and xanthan gum (1 g) were added to purified water (78.3 g), and dissolved by stirring well (Solution A). Separately, sodium benzoate (0.4 g) and sodium edetate (EDTA-Na) (0.04 g) were added to water (9.56 g), and dissolved by stirring well (Solution B). Separately, hydroxypropylmethyl cellulose (1 g) (HPMC; hypromellose 2910) and citric acid hydrate (1 g) were added to water (28.0 g), and dissolved by stirring well (Solution C). After adding Solution B and Solution C to Solution A, and stirring the mixture well, particles (0.3 g) (spray-dried product; tolvaptan SD powder) containing amorphous tolvaptan including tolvaptan and hydroxypropylmethyl cellulose (HPMC; hypromellose 2910) in a weight ratio of 2:1 were added thereto, and dispersed by stirring well.

Preparation Example 4B

Suspension: HPMC-SD

Xylitol (80 g), sucralose (0.4 g), and xanthan gum (1 g) were added to purified water (78.2 g), and dissolved by stirring well (Solution A). Separately, sodium benzoate (0.4 g) and sodium edetate (EDTA-Na) (0.04 g) were added to water (9.56 g), and dissolved by stirring well (Solution B).

Separately, hydroxypropylmethyl cellulose (1 g) (HPMC; hypromellose 2910) and citric acid hydrate (1 g) were added to water (28.0 g), and dissolved by stirring well (Solution C). After adding Solution B and Solution C to Solution A, and stirring the mixture well, particles (0.4 g) (spray-dried product; tolvaptan SD powder) containing amorphous tolvaptan including tolvaptan and hydroxypropylmethyl cellulose (HPMC; hypromellose 2910) in a weight ratio of 1:1 were added thereto, and dispersed by stirring well.

Table 3 shows the component composition of the formulations prepared in Preparation Examples 4A and 4B. All figures are expressed in wt %.

TABLE 3

| Component | Preparation Example 4A (HPC-SD) | Preparation Example 4B (HPMC-SD) |
| --- | --- | --- |
| Tolvaptan SD powder (Tolvaptan:HPC = 2:1) | 0.15 | — |
| Tolvaptan SD powder (Tolvaptan:HPMC = 1:1) | — | 0.20 |
| Xylitol | 40.00 | 40.00 |
| Sucralose | 0.20 | 0.20 |
| Xanthan gum | 0.50 | 0.50 |
| HPMC | 0.50 | 0.50 |
| Sodium benzoate | 0.20 | 0.20 |
| EDTA•2Na | 0.02 | 0.02 |
| Citric acid hydrate | 0.50 | 0.50 |
| Purified water | 57.93 | 57.88 |
| Total | 100.00 | 100.00 |

The thus-prepared formulations of Preparation Examples 4A and 4B were subjected to a dissolution test according to the second method (paddle method) of the Japanese Pharmacopoeia dissolution test immediately after production, and after 4 weeks and 8 weeks of storage at 40° C. The conditions of the dissolution test were the same as those in Test Example 1. FIGS. 7 and 8 show the results.

FIGS. 7 and 8 indicate that crystallization of amorphous tolvaptan was efficiently suppressed in the suspension containing particles including HPC-containing amorphous tolvaptan, and the suspension containing particles including HPMC-containing amorphous tolvaptan after 4 weeks of storage at 40° C. In particular, it was confirmed that the suspension containing particles including HPMC-containing amorphous tolvaptan can maintain its amorphous tolvaptan about twice as long as the suspension containing particles including HPC-containing amorphous tolvaptan.

Test Example 5

Dissolution and PK Profile

Preparation Example 5A

Tablet, 3.75 mg

Particles (28.2 g) (spray-dried product; tolvaptan SD powder) containing amorphous tolvaptan including tolvaptan and hydroxypropyl cellulose (HPC; HPC-SL) in a weight ratio of 2:1, lactose (291.9 g), corn starch (50.0 g), and crystalline cellulose (50.0 g) were mixed. The obtained mixture was introduced into a tumbling fluidized bed granulating dryer (produced by Powrex Corporation, Multiplex MP-01). Using a hydroxypropyl cellulose (HPC; HPC-L) 5 w/w % aqueous solution (200 g), fluidized bed granulation and drying were performed to obtain granules. Hydroxypropyl cellulose (LH-11) with a low substitution degree (22.5 g) and magnesium stearate (5.0 g) were mixed with the resulting granules to form granules for tableting. Using a rotary continuous tableting machine (produced by Kikusui Seisakusho Ltd., 12HUK-AWC) at a tableting pressure of 1,000 kg and a rotation number of 40 rpm, the granules were formed into a planar shape with a diameter of 6 mm and a weight of about 91.5 mg, including 3.75 mg of tolvaptan.

Preparation Example 5B

Suspension: HPC-SD Powder+0.1% Gellan Gum

Xylitol (80 g) and gellan gum (0.2 g) were added to purified water (79.5 g), and dissolved by stirring well (Solution A). Separately, sodium benzoate (0.4 g) and sodium edetate (EDTA-Na) (0.02 g) were added to water (9.58 g), and dissolved by stirring well (Solution B). Separately, hydroxypropylmethyl cellulose (0.6 g) (HPMC; hypromellose 2910) and citric acid hydrate (0.6 g) were added to water (28.8 g), and dissolved by stirring well (Solution C). After adding Solution B and Solution C to Solution A, and stirring the mixture well, particles (0.3 g) (spray-dried product; tolvaptan SD powder) containing amorphous tolvaptan including tolvaptan and hydroxypropyl cellulose (HPC; HPC-SL) in a weight ratio of 2:1 were added thereto, and dispersed by stirring well.

Preparation Example 5C

Suspension: HPC-SD Powder+0.5% Xanthan Gum

Xylitol (80 g), sucralose (0.4 g), and xanthan gum (1 g) were added to purified water (78.3 g), and dissolved by stirring well (Solution A). Separately, sodium benzoate (0.4 g) and sodium edetate (EDTA-Na) (0.04 g) were added to water (9.56 g), and dissolved by stirring well (Solution B). Separately, hydroxypropylmethyl cellulose (1 g) (HPMC; hypromellose 2910) and citric acid hydrate (1 g) were added to water (28.0 g), and dissolved by stirring well (Solution C). After adding Solution B and Solution C to Solution A, and stirring the mixture well, particles (0.3 g) (spray-dried product; tolvaptan SD powder) containing amorphous tolvaptan including tolvaptan and hydroxypropyl cellulose (HPC; HPC-SL) in a weight ratio of 2:1 were added thereto, and dispersed by stirring well.

Preparation Example 5D

Suspension: HPMC-SD Powder+0.5% Xanthan Gum

Xylitol (80 g), sucralose (0.4 g), and xanthan gum (1 g) were added to purified water (78.2 g), and dissolved by stirring well (Solution A). Separately, sodium benzoate (0.4 g) and sodium edetate (EDTA-Na) (0.04 g) were added to water (9.56 g), and dissolved by stirring well (Solution B). Separately, hydroxypropylmethyl cellulose (1 g) (HPMC; hypromellose 2910) and citric acid hydrate (1 g) were added to water (28.0 g), and dissolved by stirring well (Solution C). After adding Solution B and Solution C to Solution A, and stirring the mixture well, particles (0.4 g) (spray-dried product; tolvaptan SD powder) containing amorphous tolvaptan including tolvaptan and hydroxypropyl cellulose (HPC; HPC-SL) in a weight ratio of 1:1 were added thereto, and dispersed by stirring well.

Table 4 shows the component compositions of the formulations prepared in Preparation Examples 5B to 5D. All figures are expressed in wt %.

TABLE 4

| Component | Preparation Example 5B 0.1% Gellan gum stored at 2 to 8° C. for 2 weeks | Preparation Example 5C 0.5% Xanthan gum stored at 2 to 8° C. for 2 weeks | Preparation Example 5D 0.5% Xanthan gum stored at 2 to 8° C. for 2 weeks |
|---|---|---|---|
| Tolvaptan SD powder (Tolvaptan:HPC = 2:1) | 0.15 | 0.15 | — |
| Tolvaptan SD powder (Tolvaptan:HPMC = 1:1) | — | — | 0.20 |
| Xylitol | 40.0 | 40.0 | 40.0 |
| Sucralose | — | 0.20 | 0.20 |
| Gellan gum | 0.10 | — | — |
| Xanthan gum | — | 0.50 | 0.50 |
| HPMC | 0.30 | 0.50 | 0.50 |
| Sodium benzoate | 0.20 | 0.20 | 0.20 |
| EDTA•2Na | 0.01 | 0.02 | 0.02 |
| Citric acid hydrate | 0.30 | 0.50 | 0.50 |
| Purified water | 59.1 | 57.9 | 57.9 |
| Total | 100.0 | 100.0 | 100.0 |

(1) Dissolution Profile

After the thus-prepared formulation of Preparation Example 5A was stored at room temperature for 2 years, or after the thus-prepared formulations of Preparation Examples 5B to 5D were stored at 2 to 8° C. for 2 weeks, a dissolution test according to the second method (paddle method) of the Japanese Pharmacopoeia dissolution test was performed. The conditions of the dissolution test were the same as those in Test Example 1. FIG. 9 shows the results.

FIG. 9 indicates that crystallization of amorphous tolvaptan was efficiently suppressed and a high dissolution rate was maintained in the formulations of Preparation Examples 5B to 5D of the present invention.

(2) PK Profile

Each of the thus-prepared formulations of Preparation Examples 5A to 5D was loaded into an individual gelatin capsule. Immediately after forced oral administration of the capsule to a fasted male beagle dog, a 0.1N HCl aqueous solution was forcedly orally administered. 0.5, 1, 2, 3, 4, 6, 8, and 12 hours after administration, about 0.5 mL of blood was collected from a forelimb vein. The collected bloods were each introduced into individual Separapid tubes, and allowed to stand for about 30 minutes at room temperature. Centrifugation was then performed at 1800×g for 10 minutes to obtain serums. The obtained blood serums were stored at −20° C. or less until measurement. The tolvaptan concentration in each of the obtained serums was measured by LC-MS/MS.

FIG. 10 indicates that the formulations of Preparation Examples 5B to 5D of the present invention showed almost the same PK profile as the tablets (control). Thus, there was considered to be almost no crystallization of amorphous tolvaptan caused by drug administration.

Test Example 6

Dissolution Test and Content Uniformity Test of Suspension Formulation

Preparation Example 6A

Suspension: SD Powder Containing Tolvaptan Alone, 0% HPMC

Sucralose (0.6 g) and citric acid hydrate (1.5 g) were added to purified water (282.6 g), and dissolved by stirring well (Solution A). Separately, sodium benzoate (0.6 g) and sodium edetate (0.06 g) were added to water (14.34 g), and dissolved by stirring well (Solution B). A liquid (79.92 g) obtained by adding Solution B to Solution A and stirring the mixture well was weighed in a different container. Amorphous tolvaptan particles (spray-dried product: SD powder containing tolvaptan alone) (0.08 g) were added thereto and dispersed by stirring well.

Preparation Example 6B

Suspension: SD Powder Containing Tolvaptan Alone, 1% HPMC

Hydroxypropylmethyl cellulose (HPMC; hypromellose 2910: TC-5E) (3 g), sucralose (0.6 g), and citric acid hydrate (1.5 g) were added to purified water (279.6 g), and dissolved by stirring well (Solution A). Separately, sodium benzoate (0.6 g) and sodium edetate (0.06 g) were added to water (14.34 g), and dissolved by stirring well (Solution B). A liquid (79.92 g) obtained by adding Solution B to Solution A, and stirring the mixture well was weighed in a different container. Amorphous tolvaptan particles (spray-dried product; SD powder containing tolvaptan alone) (0.08 g) were added thereto, and dispersed by stirring well.

Preparation Example 6C

Suspension: SD Powder Containing Tolvaptan Alone, 3% HPMC

Hydroxypropylmethyl cellulose (HPMC; hypromellose 2910: TC-5E) (9 g), sucralose (0.6 g), and citric acid hydrate (1.5 g) were added to purified water (273.6 g), and dissolved by stirring well (Solution A). Separately, sodium benzoate (0.6 g) and sodium edetate (0.06 g) were added to water (14.34 g), and dissolved by stirring well (Solution B). A liquid (79.92 g) obtained by adding Solution B to Solution A and stirring the mixture well was weighed in a different container; and amorphous tolvaptan particles (spray-dried product; SD powder containing tolvaptan alone) (0.08 g) were added thereto, and dispersed by stirring well.

Preparation Example 6D

Suspension: SD Powder of Tolvaptan/HPC-SL, 1% HPMC

Hydroxypropylmethyl cellulose (HPMC; hypromellose 2910: TC-5E) (3 g), sucralose (0.6 g) and citric acid hydrate (1.5 g) were added to purified water (279.3 g), and dissolved by stirring well (Solution A). Separately, sodium benzoate (0.6 g) and sodium edetate (0.06 g) were added to water (14.34 g), and dissolved by stirring well (Solution B). A liquid (79.84 g) obtained by adding Solution B to Solution A and stirring the mixture well was weighed in a different container. Particles (spray-dried product; SD powder of tolvaptan/HPC-SL) (0.16 g) (0.08 g as tolvaptan) containing amorphous tolvaptan including tolvaptan and hydroxypropyl cellulose (HPC; HPC-SL) in a weight ratio of 1:1 were added thereto, and dispersed by stirring well.

Preparation Example 6E

Suspension: SD Powder of Tolvaptan/TC-5E, 0.9% HPMC

Hydroxypropylmethyl cellulose (HPMC; hypromellose 2910:TC-5E) (2.7 g), sucralose (0.6 g), and citric acid hydrate (1.5 g) were added to purified water (279.6 g), and dissolved by stirring well (Solution A). Separately, sodium benzoate (0.6 g) and sodium edetate (0.06 g) were added to water (14.34 g), and dissolved by stirring well (Solution B). A liquid (79.84 g) obtained by adding Solution B to Solution A and stirring the mixture well was weighed in a different container. Particles (spray-dried product; SD powder of tolvaptan/TC-5E) (0.16 g) (0.08 g as tolvaptan) containing amorphous tolvaptan including tolvaptan and hydroxypropylmethyl cellulose (HPMC; hypromellose 2910:TC-5E) in a weight ratio of 1:1 were added thereto, and dispersed by stirring well.

Preparation Example 6F

Suspension: SD Powder of Tolvaptan/TC-5E, 1% HPMC, 30% Sorbitol

Sorbitol (180 g) and sucralose (1.2 g) were added to purified water (297.6 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910:TC-5E) (6 g) and citric acid hydrate (3 g) were added to water (81 g), and dissolved by stirring well (Solution C). A liquid (249.5 g) obtained by adding Solution B and Solution C to Solution A and stirring the mixture well was weighed in a different container. Particles containing amorphous tolvaptan (spray-dried product; SD powder of tolvaptan/TC-5E) (0.5 g) (0.25 g as tolvaptan) including tolvaptan and hydroxypropylmethyl cellulose (HPMC; hypromellose 2910:TC-5E) in a weight ratio of 1:1 was added thereto, and dispersed by stirring well.

Preparation Example 6G

Suspension: SD Powder of Tolvaptan/TC-5E, 1% HPMC, 45% Sorbitol

Sorbitol (270 g) and sucralose (1.2 g) were added to purified water (207.6 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910:TC-5E) (6 g) and citric acid hydrate (3 g) were added to water (81 g), and dissolved by stirring well (Solution C). A liquid (249.5 g) obtained by adding Solution B and Solution C to Solution A and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910:TC-5E) in a weight ratio of 1:1 were added thereto, and dispersed by stirring well.

Preparation Example 6H

Suspension: SD Powder of Tolvaptan/TC-5E, 1% HPMC, 60% Sorbitol

Sorbitol (360 g) and sucralose (1.2 g) were added to purified water (117.6 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910:TC-5E) (6 g) and citric acid hydrate (3 g) were added to water (81 g), and dissolved by stirring well (Solution C). A liquid (249.5 g) obtained by adding Solution B and Solution C to Solution A and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910:TC-5E) in a weight ratio of 1:1 were added thereto, and dispersed by stirring well.

Preparation Example 6I

Suspension: SD Powder of Tolvaptan/TC-5E, 1% HPMC, 45% Sorbitol

Sorbitol (270 g) and sucralose (1.2 g) were added to purified water (207.48 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910:TC-5E) (6 g) and citric acid hydrate (3 g) were added to water (81 g), and dissolved by stirring well (Solution C). A liquid (249.5 g) obtained by adding Solution B, Solution C, and cherry flavor (0.12 g) to Solution A and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910:TC-5E) in a weight ratio of 1:1 were added thereto, and dispersed by stirring well.

Preparation Example 6J

Suspension: SD Powder of Tolvaptan/TC-5E, 1% HPMC, 0% Sorbitol

Gellan gum (0.6 g) and sucralose (1.2 g) were added to purified water (476.88 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910:TC-5E) (6 g) and citric acid hydrate (3 g) were added to water (81 g), and dissolved by stirring well (Solution C). A liquid (249.5 g) obtained by adding Solution B, Solution C, and cherry flavor (0.12 g) to Solution A and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910:TC-5E) in a weight ratio of 1:1 were added thereto, and dispersed by stirring well.

Preparation Example 6K

Suspension: SD Powder of Tolvaptan/TC-5E, 1% HPMC, 0% Sorbitol

Carrageenan (3 g) and sucralose (1.2 g) were added to purified water (474.48 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910:TC-5E) (6 g) and citric acid hydrate (3 g) were added to water (81 g), and dissolved by stirring well (Solution C). A liquid (249.5 g) obtained by adding Solution B, Solution C, and cherry flavor (0.12 g) to Solution A and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910:TC-5E) in a weight ratio of 1:1 were added thereto, and dispersed by stirring well.

Preparation Example 6L

Suspension: SD Powder of Tolvaptan/TC-5E, 1% HPMC, 0% Sorbitol, 0.5% Carboxyvinyl Polymer Carboxyvinyl polymer (3 g) and sucralose (1.2 g) were added to purified water (474.48 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910:TC-5E) (6 g) and citric acid hydrate (3 g) were added to water (81 g), and dissolved by stirring well (Solution C). A liquid (249.5 g) obtained by adding Solution B, Solution C, and cherry flavor (0.12 g) to Solution A and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910: TC-5E) in a weight ratio of 1:1 were added thereto, and dispersed by stirring well.

Preparation Example 6M

Suspension: SD Powder of Tolvaptan/TC-5E, 1% HPMC, 0% Sorbitol, 0.5% Xanthan Gum Xanthan gum (3 g) and sucralose (1.2 g) were added to purified water (474.48 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910: TC-5E) (6 g) and citric acid hydrate (3 g) were added to water (81 g), and dissolved by stirring well (Solution C). A liquid (249.5 g) obtained by adding Solution B, Solution C, and cherry flavor (0.12 g) to Solution A and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910: TC-5E) in a weight ratio of 1:1 were added thereto, and dispersed by stirring well.

Preparation Example 6N

Suspension: SD Powder of Tolvaptan/TC-5E, 1% HPMC, 15% Sorbitol, 0.3% Xanthan Gum Sorbitol (90 g), xanthan gum (1.8 g), and sucralose (1.2 g) were added to purified water (385.68 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910: TC-5E) (6 g) and citric acid hydrate (3 g) were added to water (81 g), and dissolved by stirring well (Solution C). A liquid (249.5 g) obtained by adding Solution B, Solution C, and cherry flavor (0.12 g) to Solution A and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910:TC-5E) in a weight ratio of 1:1 were added thereto, and dispersed by stirring well.

Preparation Example 6O

Suspension: SD Powder of Tolvaptan/TC-5E, 1% HPMC, 15% Sorbitol, 0.5% Xanthan Gum Sorbitol (90 g), xanthan gum (3 g), and sucralose (1.2 g) were added to purified water (384.48 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910:TC-5E) (6 g) and citric acid hydrate (3 g) were added to water (81 g), and dissolved by stirring well (Solution C). A liquid (249.5 g) obtained by adding Solution B, Solution C, and cherry flavor (0.12 g) to Solution A and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910: TC-5E) in a weight ratio of 1:1 were added thereto, and dispersed by stirring well.

Preparation Example 6P

Suspension: SD Powder of Tolvaptan/TC-5E, 1% HPMC, 30% Sorbitol, 0.3% Xanthan Gum Sorbitol (180 g), xanthan gum (1.8 g), and sucralose (1.2 g) were added to purified water (295.68 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910: TC-5E) (6 g) and citric acid hydrate (3 g) were added to water (81 g) and dissolved by stirring well (Solution C). A liquid (249.5 g) obtained by adding Solution B, Solution C, and cherry flavor (0.12 g) to Solution A, and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910:TC-5E) in a weight ratio of 1:1 were added thereto, and dispersed by stirring well.

Preparation Example 6Q

Suspension: SD Powder of Tolvaptan/TC-5E, 1% HPMC, 30% Sorbitol, 0.5% Xanthan Gum Sorbitol (180 g), xanthan gum (3 g), and sucralose (1.2 g) were added to purified water (294.48 g), and dissolved by stirring well (Solution A). Separately, sodium benzoate (1.2 g) and sodium edetate (0.12 g) were added to water (28.68 g) and dissolved by stirring well (Solution B). Separately, hydroxypropylmethyl cellulose (HPMC; hypromellose 2910:TC-5E) (6 g) and citric acid hydrate (3 g) were added to water (81 g), and dissolved by stirring well (Solution C). A liquid (249.5 g) obtained by adding Solution B, Solution C, and cherry flavor (0.12 g) to Solution A and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910:TC-5E) in a weight ratio of 1:1 were added thereto, and dispersed by stirring well.

Preparation Example 6R

Suspension: SD Powder of Tolvaptan/TC-5E, 1% HPMC, 45% Sorbitol, 0.5% Xanthan Gum Sorbitol (270 g), xanthan gum (3 g), and sucralose (1.2 g) were added to purified water (204.48 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910:TC-5E) (6 g) and citric acid hydrate (3 g) were added to water (81 g), and dissolved by stirring well (Solution C). A liquid (249.5 g) obtained by adding Solution B, Solution C, and cherry flavor (0.12 g) to Solution A and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910:TC-5E) in a weight ratio of 1:1 were added thereto, and dispersed by stirring well.

Preparation Example 6S

Suspension: SD Powder of Tolvaptan/TC-5E, 1% HPMC, 45% Sorbitol, 0.1% Xanthan Gum Sorbitol (270 g), xanthan gum (0.6 g), and sucralose (1.2 g) were added to purified water (206.88 g), and dissolved by stirring well (Solution A). Separately, sodium benzoate (1.2 g) and sodium edetate (0.12 g) were added to water (28.68 g), and dissolved by stirring well (Solution B). Separately, hydroxypropylmethyl cellulose (HPMC; hypromellose 2910: TC-5E) (6 g) and citric acid hydrate (3 g) were added to water (81 g), and dissolved by stirring well (Solution C). A liquid (249.5 g) obtained by adding Solution B, Solution C, and cherry flavor (0.12 g) to Solution A and stirring the mixture well was weighed in a different container. Particles (spray-dried product; SD powder of tolvaptan/TC-5E) (0.5 g) (0.25 g as tolvaptan) containing amorphous tolvaptan including tolvaptan and hydroxypropylmethyl cellulose (HPMC; hypromellose 2910:TC-5E) in a weight ratio of 1:1 were added thereto, and dispersed by stirring well.

Table 5 shows the component compositions of the formulations prepared in Preparation Examples 6A to 6S. All figures are expressed in wt %.

TABLE 5

| | Preparation Example | | 6A | 6B | 6C | 6D | 6E | 6F | 6G | 6H | 6I | 6J |
|---|---|---|---|---|---|---|---|---|---|---|---|---|
| Component Composition [wt %] | Active Ingredient (Tolvaptan) | SD Powder (Drug Alone) | 0.10 | 0.10 | 0.10 | 0.00 | 0.00 | 0.00 | 0.00 | 0.00 | 0.00 | 0.00 |
| | | SD Powder (Drug/HPC-SL = 1/1) | 0.00 | 0.00 | 0.00 | 0.20 | 0.00 | 0.00 | 0.00 | 0.00 | 0.00 | 0.00 |
| | | SD Powder (Drug/TC-5E = 1/1) | 0.00 | 0.00 | 0.00 | 0.00 | 0.20 | 0.20 | 0.20 | 0.20 | 0.20 | 0.20 |
| | Suspending Agent | Gellan Gum | 0.00 | 0.00 | 0.00 | 0.00 | 0.00 | 0.00 | 0.00 | 0.00 | 0.00 | 0.10 |
| | | Carrageenan | 0.00 | 0.00 | 0.00 | 0.00 | 0.00 | 0.00 | 0.00 | 0.00 | 0.00 | 0.00 |
| | | Carboxyvinyl Polymer | 0.00 | 0.00 | 0.00 | 0.00 | 0.00 | 0.00 | 0.00 | 0.00 | 0.00 | 0.00 |
| | | Xanthan Gum | 0.00 | 0.00 | 0.00 | 0.00 | 0.00 | 0.00 | 0.00 | 0.00 | 0.00 | 0.00 |
| | HPMC | Hypromellose 2910 (TC-5E) | 0.00 | 1.00 | 3.00 | 1.00 | 0.90 | 1.00 | 1.00 | 1.00 | 1.00 | 1.00 |
| | Sweetener | Sorbitol | 0.00 | 0.00 | 0.00 | 0.00 | 0.00 | 30.0 | 45.0 | 60.0 | 45.0 | 0.00 |
| | | Sucralose | 0.20 | 0.20 | 0.20 | 0.20 | 0.20 | 0.20 | 0.20 | 0.20 | 0.20 | 0.20 |
| | Stabilizer | Sodium Edetate | 0.02 | 0.02 | 0.02 | 0.02 | 0.02 | 0.02 | 0.02 | 0.02 | 0.02 | 0.02 |
| | Preservative | Sodium Benzoate | 0.20 | 0.20 | 0.20 | 0.20 | 0.20 | 0.20 | 0.20 | 0.20 | 0.20 | 0.20 |
| | pH-adjusting Agent | Citric Acid Hydrate | 0.50 | 0.50 | 0.50 | 0.50 | 0.50 | 0.50 | 0.50 | 0.50 | 0.50 | 0.50 |
| | Flavoring Agent | Cherry Flavor | 0.00 | 0.00 | 0.00 | 0.00 | 0.00 | 0.00 | 0.00 | 0.00 | 0.02 | 0.02 |
| | Solvent | Purified Water | 99.0 | 98.0 | 96.0 | 97.9 | 98.0 | 67.9 | 52.9 | 37.9 | 52.9 | 97.8 |
| Dissolution Rate (60 Min. Value) [%] | Immediately After Production (at the Time of Start) | | 89.9 | 97.0 | 97.0 | 103.6 | 105.1 | 95.6 | 91.4 | 93.5 | 93.2 | 92.7 |
| | 5° C. | 1 W | 9.4 | 97.6 | 97.0 | 98.9 | 100.4 | 92.6 | 92.0 | 92.3 | 95.5 | 86.3 |
| | | 2 W | 7.6 | 96.4 | 98.8 | 105.3 | 101.6 | 96.1 | 90.2 | 90.0 | 93.2 | 95.1 |

| | Preparation Example | | 6K | 6L | 6M | 6N | 6O | 6P | 6Q | 6R | 6S |
|---|---|---|---|---|---|---|---|---|---|---|
| Component Composition [wt %] | Active Ingredient (Tolvaptan) | SD Powder (Drug Alone) | 0.00 | 0.00 | 0.00 | 0.00 | 0.00 | 0.00 | 0.00 | 0.00 | 0.00 |
| | | SD Powder (Drug/HPC-SL = 1/1) | 0.00 | 0.00 | 0.00 | 0.00 | 0.00 | 0.00 | 0.00 | 0.00 | 0.00 |

TABLE 5-continued

| | | | | | | | | | | | |
|---|---|---|---|---|---|---|---|---|---|---|---|
| | | SD Powder (Drug/TC-5E = 1/1) | 0.20 | 0.20 | 0.20 | 0.20 | 0.20 | 0.20 | 0.20 | 0.20 | 0.20 |
| | Suspending Agent | Gellan Gum | 0.00 | 0.00 | 0.00 | 0.00 | 0.00 | 0.00 | 0.00 | 0.00 | 0.00 |
| | | Carrageenan | 0.50 | 0.00 | 0.00 | 0.00 | 0.00 | 0.00 | 0.00 | 0.00 | 0.00 |
| | | Carboxyvinyl Polymer | 0.00 | 0.50 | 0.00 | 0.00 | 0.00 | 0.00 | 0.00 | 0.00 | 0.00 |
| | | Xanthan Gum | 0.00 | 0.00 | 0.50 | 0.30 | 0.50 | 0.30 | 0.50 | 0.50 | 0.10 |
| | HPMC | Hypromellose 2910 (TC-5E) | 1.00 | 1.00 | 1.00 | 1.00 | 1.00 | 1.00 | 1.00 | 1.00 | 1.00 |
| | Sweetener | Sorbitol | 0.00 | 0.00 | 0.00 | 15.0 | 15.0 | 30.0 | 30.0 | 45.0 | 45.0 |
| | | Sucralose | 0.20 | 0.20 | 0.20 | 0.20 | 0.20 | 0.20 | 0.20 | 0.20 | 0.20 |
| | Stabilizer | Sodium Edetate | 0.02 | 0.02 | 0.02 | 0.02 | 0.02 | 0.02 | 0.02 | 0.02 | 0.02 |
| | Preservative | Sodium Benzoate | 0.20 | 0.20 | 0.20 | 0.20 | 0.20 | 0.20 | 0.20 | 0.20 | 0.20 |
| | pH-adjusting Agent | Citric Acid Hydrate | 0.50 | 0.50 | 0.50 | 0.50 | 0.50 | 0.50 | 0.50 | 0.50 | 0.50 |
| | Flavoring Agent | Cherry Flavor | 0.02 | 0.02 | 0.02 | 0.02 | 0.02 | 0.02 | 0.02 | 0.02 | 0.02 |
| | Solvent | Purified Water | 97.4 | 97.4 | 97.4 | 82.6 | 82.4 | 67.6 | 67.4 | 52.4 | 52.8 |
| Dissolution Rate (60 Min. Value) [%] | Immediately After Production (at the Time of Start) | | 95.8 | 77.0 | 93.7 | 94.1 | 90.3 | 94.5 | 94.1 | 92.0 | 93.1 |
| | 5° C. | 1 W | 95.8 | 85.1 | 93.7 | 89.4 | 89.7 | 92.2 | 94.7 | 90.3 | 91.3 |
| | | 2 W | 95.2 | 86.9 | 89.6 | 93.0 | 90.3 | 92.2 | 94.1 | 89.7 | 93.7 |

(1) Dissolution Test Results

The thus-prepared formulations of Preparation Examples 6A to 6S were subjected to a dissolution test according to the second method (paddle method) of the Japanese Pharmacopoeia dissolution test immediately after production, and after 1 week and 2 weeks of storage at 5° C. The conditions of the dissolution test were the same as those in Test Example 1. FIG. 11 shows the dissolution profile of Preparation Example 6A. Table 5 shows the measurement results of the dissolution rate of the 60 min. value.

FIG. 11 indicates that the dissolution rate was remarkably reduced when the suspension (Preparation Example 6A) containing no HPMC in the formulation was stored at 5° C. for 1 week. In contrast, it was confirmed from Table 5 that in the formulations of Preparation Examples 6B to 6S of the present invention, which were stored at 5° C. for 2 weeks, crystallization of amorphous tolvaptan was efficiently suppressed and a high dissolution rate was maintained.

(2) Content Uniformity Test Results

Each of the formulations of Preparation Examples 6I and 6R prepared as above was weighed in a 50 mL Mighty Vial in an amount of about 40 g. After performing resuspension by shaking the vial well, the formulation was accurately weighed in an amount of 2 g from each of the upper, middle, and lower portions of the central region of the vial to measure the tolvaptan content (product immediately after preparation) using a high-speed liquid chromatograph (HPLC). Each of the remaining formulations was allowed to stand at 5° C. for 3 days; then, without shaking (resuspension), the formulation was accurately weighed in an amount of 2 g from each of the upper, middle, and lower portions of the central region of the vial. In the same manner as above, the tolvaptan content (a product stored at 5° C. for 3 days) was measured. FIGS. 12(a) and (b) show the appearance and content of the formulation immediately after preparation and the formulation stored at 5° C. for 3 days. Note that the tolvaptan content measured is indicated as a percentage based on the case in which the tolvaptan content in the formulation is 0.1% by weight.

FIGS. 12(a) and 12(b) indicate that in the suspension (Preparation Example 6I) containing no xanthan gum, amorphous tolvaptan particles surfaced after storage at 5° C. for 3 days, and the tolvaptan content in the upper portion was high. In contrast, in the suspension (Preparation Example 6R) containing 0.5% xanthan gum, the tolvaptan content remained about the same even after storage at 5° C. for 3 days, and it was confirmed that the content uniformity was ensured.

TABLE 6

| | | Immediately after preparation | |
|---|---|---|---|
| | | 6I 0% Xanthan Gum | 6R 0.5% Xanthan Gum |
| Tolvaptan Content (%) | Upper | 101.6 | 100.1 |
| | Middle | 100.1 | 99.5 |
| | Lower | 98.3 | 100.3 |

TABLE 7

| | | 5° C., After 3 days | |
|---|---|---|---|
| | | 6I 0% Xanthan Gum | 6R 0.5% Xanthan Gum |
| Tolvaptan Content (%) | Upper | 211.1 | 101.1 |
| | Middle | 42.2 | 100.3 |
| | Lower | 35.8 | 101.2 |

The invention claimed is:

1. A suspension for oral administration, comprising:
   (a) particles containing amorphous tolvaptan and a polymer;
   (b) hydroxypropyl methylcellulose (HPMC); and
   (c) a solvent,
   wherein the particles containing amorphous tolvaptan (a) exclude polyvinylpyrrolidone;
   wherein an amount of the HPMC (b) is 0.1 to 5% by weight based on a total weight of the suspension for oral administration; and
   wherein the HPMC (b) has a viscosity of 1 to 4000 mPa·s in a 2% aqueous solution at 20° C., and/or an amount of the particles containing amorphous tolvaptan (a) is 0.01 to 5% by weight based on the total weight of the suspension for oral administration.

2. The suspension for oral administration according to claim 1, wherein the polymer is at least one member selected from the group consisting of hydroxypropyl cellulose (HPC) and HPMC.

3. The suspension for oral administration according to claim 1, wherein the weight ratio of the tolvaptan to the polymer in the particles containing amorphous tolvaptan (a) is 8:1 to 1:4.

4. The suspension for oral administration according to claim 1, wherein the solvent (c) is water.

5. The suspension for oral administration according to claim 1, further comprising (d) a suspending agent and/or (e) a sweetener.

6. The suspension for oral administration according to claim 5, wherein the suspending agent (d) is at least one member selected from the group consisting of xanthan gum, gellan gum, carrageenan, carboxyvinyl polymers, and sodium carboxymethyl cellulose.

7. The suspension for oral administration according to claim 5, wherein the sweetener (e) is at least one member selected from the group consisting of mannitol, sorbitol, xylitol, maltitol, erythritol, sucrose, sucralose, aspartame, acesulfame potassium, saccharin, thaumatin, stevia extracts, trehalose, lactose, maltose, glucose, and glycerin.

8. The suspension for oral administration according to claim 1, further comprising at least one member selected from the group consisting of pH-adjusting agents, preservatives, stabilizers, and flavoring agents.

9. The suspension for oral administration according to claim 1, which is in the form of a syrup.

10. The suspension for oral administration according to claim 1, wherein the HPMC (b) has the viscosity of 1 to 4000 mPa·s in the 2% aqueous solution at 20° C.

11. The suspension for oral administration according to claim 1, wherein the amount of the particles containing amorphous tolvaptan (a) is 0.01 to 5% by weight based on the total weight of the suspension for oral administration.

12. The suspension for oral administration according to claim 10, wherein the amount of the particles containing amorphous tolvaptan (a) is 0.01 to 5% by weight based on the total weight of the suspension for oral administration.

13. A drug for preventing, reducing, or treating hyponatremia, polycystic kidney disease, body fluid retention in heart failure, or body fluid retention in liver cirrhosis comprising the suspension for oral administration according to claim 1.

14. A method for preventing, reducing, or treating hyponatremia, polycystic kidney disease, body fluid retention in heart failure, or body fluid retention in liver cirrhosis, the method comprising administering the suspension for oral administration according to claim 1 to a patient in recognized need of prevention, reduction, or treatment of hyponatremia, polycystic kidney disease, body fluid retention in heart failure, or body fluid retention in liver cirrhosis.

15. A method for producing a suspension for oral administration, the method comprising uniformly dispersing particles containing amorphous tolvaptan in an aqueous suspension containing hydroxypropyl methylcellulose (HPMC) or an aqueous solution containing HPMC,
  wherein the particles containing amorphous tolvaptan contain amorphous tolvaptan and a polymer;
  wherein the particles containing amorphous tolvaptan exclude polyvinylpyrrolidone;
  wherein an amount of the HPMC is 0.1 to 5% by weight based on a total weight of the suspension for oral administration; and
  wherein the HPMC has a viscosity of 1 to 4000 mPa·s in a 2% aqueous solution at 20° C., and/or an amount of the particles containing amorphous tolvaptan is 0.01 to 5% by weight based on the total weight of the suspension for oral administration.

16. The method according to claim 15, wherein the HPMC (b) has the viscosity of 1 to 4000 mPa·s in the 2% aqueous solution at 20° C.

17. The method according to claim 15, wherein the amount of the particles containing amorphous tolvaptan (a) is 0.01 to 5% by weight based on the total weight of the suspension for oral administration.

18. The method according to claim 16, wherein the amount of the particles containing amorphous tolvaptan (a) is 0.01 to 5% by weight based on the total weight of the suspension for oral administration.

19. A suspension for oral administration, comprising:
  (a) particles consisting of (i) amorphous tolvaptan and (ii) HPC or HPMC;
  (b) hydroxypropyl methylcellulose (HPMC); and
  (c) a solvent,
  wherein the HPMC (b) has a viscosity of 1 to 4000 mPa·s in a 2% aqueous solution at 20° C., and/or the amount of the particles containing amorphous tolvaptan (a) is 0.01 to 5% by weight based on the total weight of the suspension for oral administration.

20. The suspension for oral administration according to claim 19, wherein an amount of the HPMC (b) is 0.1 to 5% by weight based on a total weight of the suspension for oral administration.

21. The suspension for oral administration according to claim 1, wherein the polymer is at least one member selected from the group consisting of hydroxypropyl cellulose (HPC) and HPMC, and the weight ratio of the tolvaptan to the polymer in the particles containing amorphous tolvaptan (a) is 2:1 to 1:1.

\* \* \* \* \*